US006770749B2

(12) United States Patent
Ellenhorn et al.

(10) Patent No.: US 6,770,749 B2
(45) Date of Patent: Aug. 3, 2004

(54) P53-SPECIFIC T CELL RECEPTOR FOR ADOPTIVE IMMUNOTHERAPY

(75) Inventors: Joshua D. I. Ellenhorn, North Hollywood, CA (US); Don J. Diamond, Glendora, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/789,697

(22) Filed: Feb. 22, 2001

(65) Prior Publication Data

US 2002/0064521 A1 May 30, 2002

Related U.S. Application Data

(60) Provisional application No. 60/183,752, filed on Feb. 22, 2000.

(51) Int. Cl.$^7$ ................. C07H 21/04; A51K 48/00; C12N 15/63; C12N 5/08

(52) U.S. Cl. ............... 536/23.5; 536/23.1; 435/320.1; 435/455; 435/372.3; 424/93.21

(58) Field of Search .................. 536/23.1, 23.5; 435/320.1, 455, 372.3, 325, 366; 424/93.21

(56) References Cited

PUBLICATIONS

Sherman et al. Molecular analysis of antigen recognition by insulin–specific T–cell hybridomas from B6 wilid–type and bm12 mutant mice. Mol. Cell. Biol. 7:1865–1872, 1987.*
Zelenika et al. Rejection of H–Y disparate skin Grafts by Monospecific CD4+ Th1 and Th2 Cells: No requirement for CD8+ T cells or B cells. J. Immunol. 161:1868–1874, 1988.*
Liu et al. Targeting of human p53–overexpressing tumor cells by an HLA A*0201–restricted Murine T–Cell receptor expressed in Jurkat T cells. Cancer Res. 60:693–701, 2000.*
Kennell, D.E. Principles and practices of nucleic acid hybridization. In: Progr. Nucl. Acid Res. Mol. Biol. 11:259–301, 1971.*
Li et al., Adoptive T–cell immunotherapy of cancer, 1999, Cytokines, Celluar and Molecular Therapy, vol. 5, pp. 105–117.*
Rudinger, Characteristics of the amino acids as components of a peptide hormone sequence, 1976, Peptide Hormones, 1–7.*
Ngo et al., Computational complexity, protein structure predicition, and the levinthal paradox, 1994, The Protein Folding Problem and Tertiary Structure Prediction, pp. 491–495.*
Riddell et al., T–cell mediated rejection of gene–modified HIV–specific cytotoxic T lymphocytes in HIV–infected patients, 1996, Nature Medicine, vol. 2, pp. 216–223.*
Bertholet, S. et al., "Cytotoxic T lymphocyte responses to wild–type and mutant mouse p53 peptides," *Eur. J. Immunol.* 27:798–801(1997).

Chikamatsu, K. et al., "Generation of anti–p53 cytotoxic T lymphocytes from human peripheral blood using autologous dendritic cells," *Clin. Cancer Res.* 5:1281–1288 (1999.
Chung, S. et al., "Functional three–domain single–chain T–cell receptors," *Proc. Natl Acad Sci USA* 91:12654–12658 (1994).
Cole, D.J. et al. "Characterization of the functional specificity of a cloned T–cell receptor heterodimer recognizing the MART–1 melanoma antigen," *Cancer Res.* 55:748–752 (1995).
Eshhar, Z. et al., "Specific activation and targeting of cytotoxic lymphocytes through chimeric single chains consisting of antibody–binding domains and the Γ or ζ subunits of the immunoglobulin and T–cell receptors," *Proc Natl Acad Sci USA* 90:720–724 (1993).
Goverman, J. et al., "Chimeric immunoglobulin–T cell receptor proteins form functional receptors: Implications for T cell receptor complex formation and activation," *Cell* 60:929–939 (1990).
Hekele, A. et al., "Growth retardation of tumors by adoptive transfer of cytotoxic T lymphocytes reprogrammed by CD44V6–specific SCV:ζ–chimera,"*Int. J. Cancer* 68:232–238 (1996).
Houbiers, J.G.A. et al., "In vitro induction of human cytotoxic T lymphocyte responses against peptides of mutant and wild–type p53," *Eur. J. Immunol.* 23:2072–2077 (1993).
Maehara, Y. et al., "Clinical implications of serum anti–p53 antibodies for patients with gastric carcinoma," *Cancer, Phila.* 85:302–308 (1999).
Mayordomo. J.I. et al., "Therapy of murine tumors with p53 wild–type and mutant sequence peptide–based vaccines," *J. Exp. Med.* 183:1357–1365 (1996).
McCarty, T.M. et al., "Targeting p53 for adoptive TR–cell immunotherapy," *Cancer Res.* 58:2601–2605 (1998).*
Nijman, H.W. et al., "Characterization of cytotoxic T lymphocyte epitopes of a self–protein, p53, and non–self–protein, influenza matrix: Relationship between major histor-compatibility complex peptide binding affinity and immune responsiveness to peptides," *J. Immunotherap.* 14:121–126 (1993).*

(List continued on next page.)

*Primary Examiner*—David Guzo
*Assistant Examiner*—Quang Nguyen
(74) *Attorney, Agent, or Firm*—Rothwell, Figg, Ernst & Manbeck, P.C.

(57) ABSTRACT

The present invention relates to molecular cloning of cDNA for both A and B chains of hu p53-specific, HLA restricted mu TCR, transfer of the cDNA to hu T cells, and functional expression of the p53-specific TCR in hu CTLs. The functional expression of the mu TCR results in the recognition of endogenously processed hu p53 expressed in tumor cells. The invention thus also relates to an anti-cancer immunotherapy by the adoptive transfer of TCR gene modified autologous T cells.

8 Claims, 9 Drawing Sheets

OTHER PUBLICATIONS

Röpke, M. et al., "T cell mediated cytotoxicity against p53–protein derived peptides in bulk and limiting dilution cultures of healthy donors," *Scand. J. Immunol.* 42:98–103 (1995).*

Röpke, M. et al., "Spontaneous human squamous cell carcinomas are killed by a human cytotoxic T lymphocyte clone recognizing a wild–type recognizing a wild–type p54–derived peptide," *Proc Natl Acad Sci USA* 93:14704–14707 (1996).*

Roth, J. et al., "p53 as a target for cancer vaccines: Recombinant canarypox virus vectors expressing p53 protect mice against lethal tumor cell challenge," *Proc Natl Acad Sci USA* 93:4781–4786 (1996).*

Stenholm, A.C.O. et al., "In vivo eradication of an established human melanoma by an in vitro generated autologous cytotoxic T cell clone: a SCID mouse model," *Int. J. Cancer* 77:476–480 (1998).*

Theobald, M. et al., "Targeting p53 as a general tumor antigen," *Proc Natl Acad Sci USA* 92:11993–11997 (1995).*

Vierboom, M.P.M. et al., "Tumor eradication by wild–type p53–specific cytotoxic T lymphocytes," *J. Exp. Med.* 186:695–704 (1997).*

Yu, Z. et al., "The use of transgenic mice to generate high affinity p53 specific cytolytic T cells," *J. Surg. Res.* 69:337–343 (1997).*

* cited by examiner

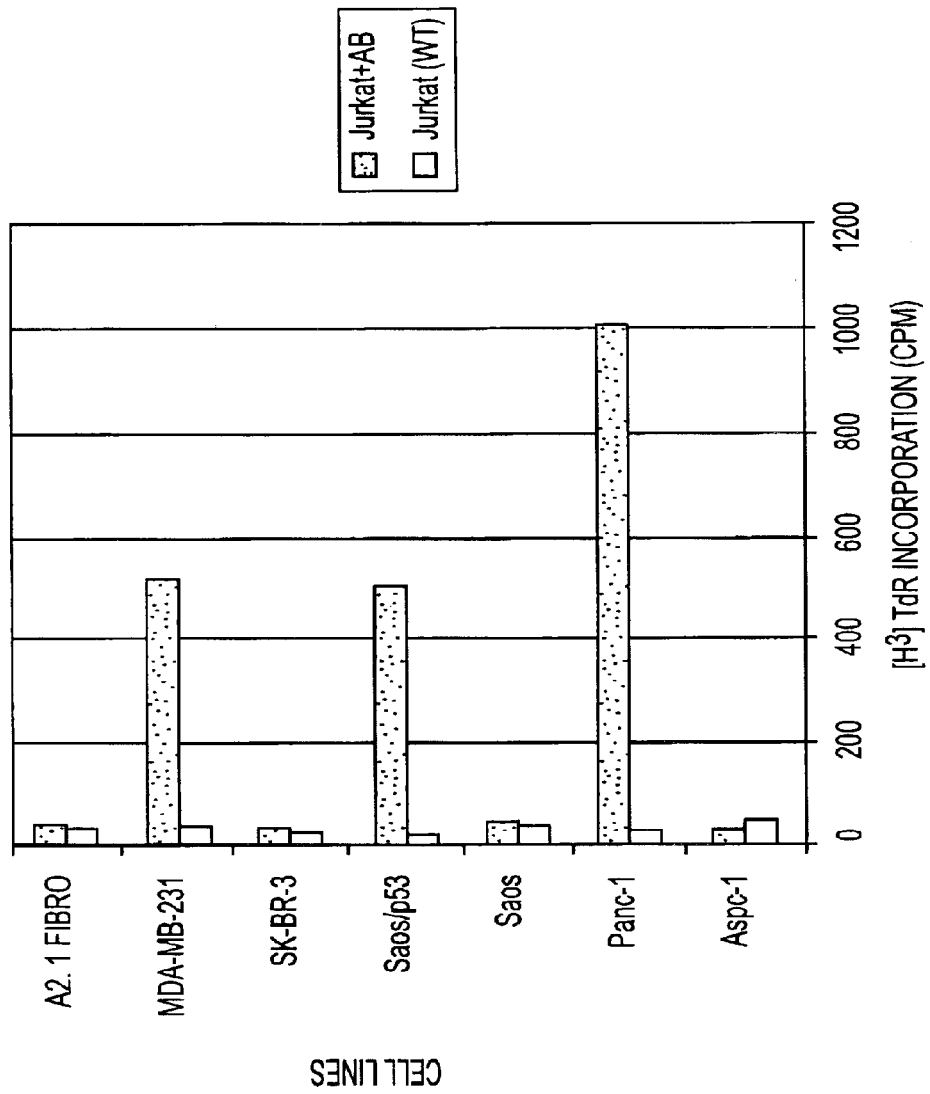

P53-SPECIFIC T CELL RECEPTOR FOR ADOPTIVE IMMUNOTHERAPY

CROSS-REFERENCE TO RELATED APPLICATION

The present application claims priority to U.S. provisional patent application Ser. No. 60/183,752 filed on Feb. 22, 2000, incorporated herein by reference.

This invention was made in the course of research funded in part by grant number CA70819 from the United States National Institutes of Health. The United States government has certain rights in the invention.

BACKGROUND OF THE INVENTION

The present invention relates to the molecular cloning of cDNA for both A and B chains of human (hu) p53-specific, HLA restricted murine (mu) T-cell receptor (TCR), transfer of the cDNA to hu T cells, and functional expression of the p53-specific TCR in hu cytotoxic T lymphocytes (CTLs). The functional expression of the mu TCR results in the recognition of endogenously processed hu p53 expressed in tumor cells. The invention thus also relates to an anti-cancer immunotherapy by the adoptive transfer of TCR gene modified autologous T cells.

The publications and other materials used herein to illuminate the background of the invention or provide additional details respecting the practice, are incorporated by reference.

p53 acts as a checkpoint for cell division in most eukaryotic cells, and is normally expressed at low levels with rapid decay kinetics. Mutations in p53 characterize a large proportion of human (hu) solid tumors. These mutations, which abrogate the function of p53 as a suppresser of cell division (Finlay et al., Cell, 57:1083–1093, 1989) are associated with a prolonged half life and much higher nuclear and cytoplasmic concentration of the p53 protein (Eliyahu et al., Proc Natl Acad Sci USA, 86:8763–8767, 1989). The mutations are generally single base missense mutations (Kovach et al., Proc Natl Acad Sci USA, 93:1093–1096, 1996 ID), and the remainder of the over-expressed p53 molecule is wild type (wt). Unfortunately, the immune response to most tumors which aberrantly express p53 is not adequate to prevent their un-restricted growth. Either tolerance or other immune-based selective mechanisms may be responsible for inadequate host defense against these tumors.

Because the p53 gene product is over-expressed in a large proportion of all solid tumors, it provides an ideal target for enhancement of the T lymphocyte anti-cancer immune response. What makes wt p53 epitopes such an attractive target for an adaptive immune response that the intracellular concentration of p53 is normally very low (Zambetti et al., FASEB J., 7:855–865, 1993), and cells expressing normal p53 at low levels will most likely escape an enhanced immune response to over-expressed p53.

Murine (mu) experimental models have clearly demonstrated the ability to target over-expressed p53 as a means of achieving tumor rejection (Roth et al., Proc Natl Acad Sci USA, 93:4781–4786, 1996) 1996; Mayordomo et al., J. Exp. Med., 183:1357–1365, 1996). Furthermore, they have established that tumor rejection can be achieved without autoreactivity to cells that express normal levels of p53 (Vierboom et al., J. Exp. Med., 186:695–704, 1997). It remains a challenge to translate these findings into an effective immunotherapy strategy for hu malignancy because of the relatively poor hu immune response to p53-overexpressing tumors (Maehara et al., Cancer, Phila. 85:302–308, 1999). By contrast, mice generate a vigorous response to both mutant and nonmutant p53 epitopes (Vierboom et al., supra; Nijman et al., 1997; Bertholet et al., Eur. J. Immunol., 27:798–801, 1997).

The T cell receptor (TCR) is the surface molecule on T cells that recognizes processed antigen, either self or allo forms. The A/B form of the TCR has been recognized as the main form that recognizes alloantigen, in contrast to the G/D form, and it initiates a cascade in which cells expressing the recognized antigen are cytolytically attacked or growth restricted by the actions of T cell-secreted lymphokines. It has been shown that adoptive immunotherapy using A/B TCR expressing cytotoxic T cells will augment the eradication of tumor in a SCID model (McCarty et al., Cancer Res., 58:2601–2605, 1998; Stenholm et al., Int. J. Cancer, 77:476–480, 1998). The capability of CTLs to cause tumor regression is thought to be far greater than a humoral response or a $CD4^+$ mediated Th infiltration of the tumor. Harnessing of the powerful anti-tumor property of CTLs has been elusive over the past 10 years; however, using gene transfer strategies with chimeric single chain TCRs provides a new approach that might overcome some of the earlier difficulties (Chung et al., Proc Natl Acad Sci USA, 91:12654–12658, 1994).

Previous studies (Yu et al., J. Surg. Res. 69:337–343, 1997) and by others (Theobald et al., Proc Natl Acad Sci USA, 92:11993–11997, 1995) have focused on immunizing transgenic (Tg) mice that express the hu transplantation antigen HLA A*0201 with immunogenic epitopes derived from wt hu p53. A potent CTL response was generated against one of these epitopes (Yu et al., supra). Isolated clonal CTLs selectively lyse/kill p53-overexpressing hu tumor cells in vitro and in in vivo tumor models in severe combined immunodeficiency (SCID) mice (McCarty et al., supra).

Consequently, it is desired to overcome the weak hu immune response to p53 by adapting to hu T cells the favorable characteristics of the powerful mu immune response to p53. It is further desired to develop compositions and methods for treating individuals having tumors which overexpress p53.

SUMMARY OF THE INVENTION

The present invention provides for the molecular cloning of cDNA for both A and B chains of hu p53-specific, HLA restricted mu TCR, the transfer of the cDNA to hu T cells, and the functional expression of the p53-specific TCR in hu CTLs. The functional expression of the mu TCR results in the recognition of endogenously processed hu p53 expressed in tumor cells. The invention thus also provides an anti-cancer immunotherapy by the adoptive transfer of TCR gene modified autologous T cells.

BRIEF DESCRIPTION OF THE FIGURES

FIG. 2A: mRNA is converted to cDNA and then dsDNA, and finally enzymatically blunt ended in steps 1–3. T4 DNA ligase is used to circularize dsDNA. Sense and antisense primers that are complementary to CA or CB gene segments that end with SalI and NotI restriction sites are used to synthesize linear DNA using PCR. These fragments are subcloned into plasmids by standard methods. FIG. 2B: The PCR fragments prepared as above were cloned into the pGEM-T vector. Plasmid DNA was isolated from individual bacterial colonies, and a portion was digested with SalI and NotI. The digested DNA was separated on a 1% agarose gel, ethidium bromide stained, and then was transferred to a nylon filter by capillary action (Southern blot). The membrane-bound DNA was hybridized with a $^{32}$P-labelled oligonucleotide (CBM or CAM), the sequence of which was identical to both mu CB genes and located within the fragment generated by the CA or CB primer sets. Plasmid DNA from several positive lanes was further analyzed by manual dideoxy sequence analysis.

FIG. 3A: Flow cytometry analysis was performed on the A parental Jurkat JRT.T3.1 line and the JRT.T3.1 transfected with the mu TCRA. The parental B JRT.T3.5 line was evaluated before and after transfection with mu B TCR cDNA. OKT3 was used to evaluate CD3 expression on both cell lines and transfectants. wt and Mu A/B TCR transfected Jurkat cells were evaluated for mu TCR expression, using mAb F23.1 (muVB8 specific). Expression was determined by flow cytometry following a phycoeryhthrin-conjugated goat antimouse immunoglobulin second step. Isotype control antibody staining of the Jurkat lines and transfectants was similar to parental line staining for the three positive cell lines. FIG. 3B: Jurkat cells that were transfected with mu A and β TCR cDNAs were evaluated for mu TCR expression by RT-PCR using CA- and CB-specific primers. Numerous lines expressing only A or B mu TCR cDNAs were generated (Lanes 2 and 3). Double transfectants (Lane 1) express both mu TCR chains. The mu p53-specific CTL line was used as a positive control, and the parental Jurkat cell line was used as a negative control. Duplicate lanes were deleted from the figure.

FIG. 4A: Supernatants were collected following incubation of the muTCR A/B transfected Jurkat cells with PBS, pp65$_{495-503}$ or p53$_{149-157}$-pulsed T2 cells. IL-2 concentration was measured as $^3$H incorporation by CTLL-2 cells, as described below in Materials and Methods. FIG. 4B: The efficiency of peptide recognition by the parental mu CTL clone 3A3/3C9 is shown. T2 cells were pulsed with p53$_{149-157}$ peptide at the indicated concentrations prior to use as target cells in a four hour CRA. The assay was conducted at an E:T of 10:1. FIG. 4C: The efficiency of peptide recognition by the mu TCR A/B transfected Jurkat cells is shown. T2 cells were pulsed with p53$_{149-157}$ peptide at the indicated concentrations prior to use as target cells in a four hour CRA. The assay was conducted as in A.

FIG. 5 shows the specific recognition of endogenously processed p53 by TCR transfected Jurkat cells. The following cell lines were used as targets: HLA A*0201 fibroblasts, breast cancer cell lines MDA-MB231 and SK-BR3, osteosarcoma line Saos p53 transfected and native, and pancreatic cancer cell lines Panc-1 and AsPC-1. IL-2 concentration was measured as $^3$H incorporation by CTLL-2, IL-2 dependent cells.

BRIEF DESCRIPTION OF THE TABLES

Figure 2A:
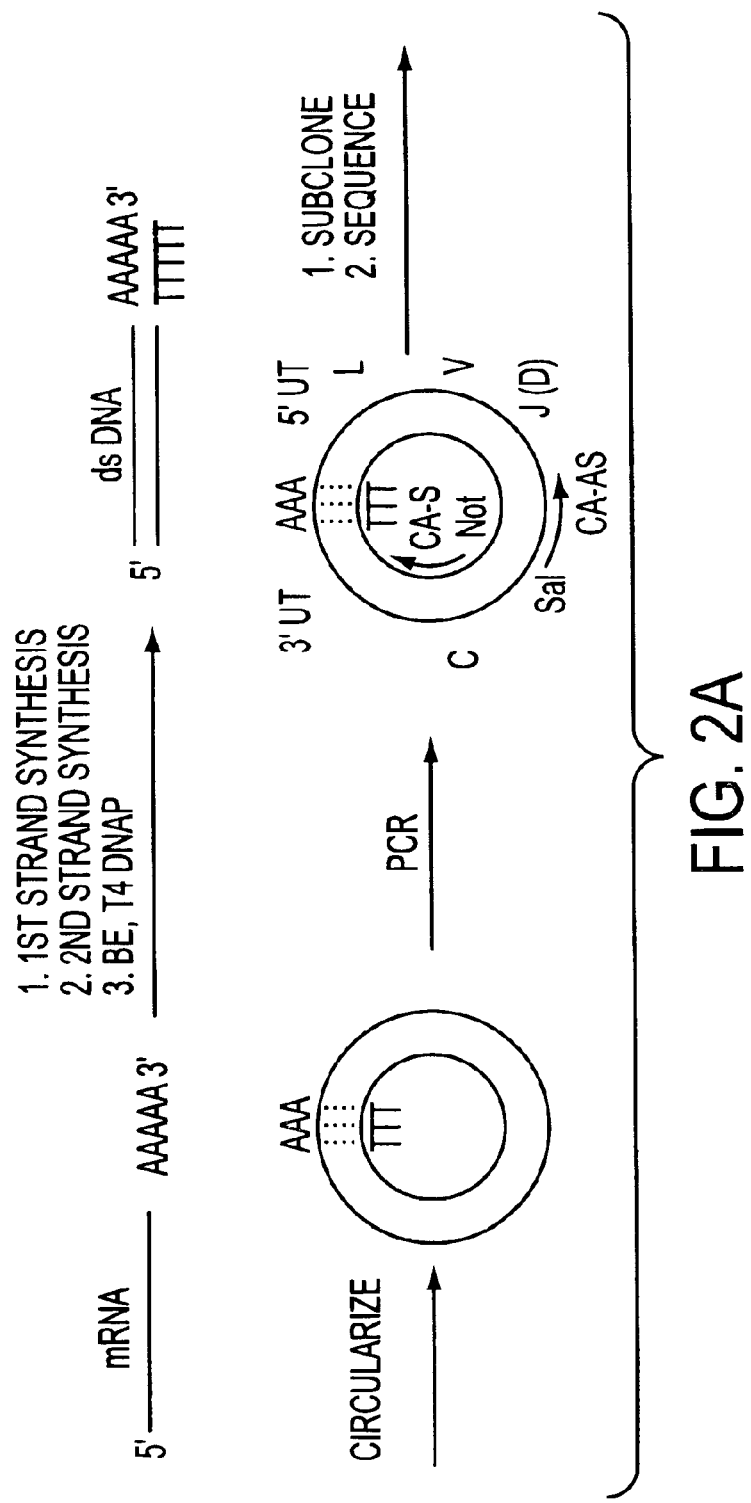
FIGS. 2A and 2B show the inverse PCR analysis of TCR usage.
Figure 2B:
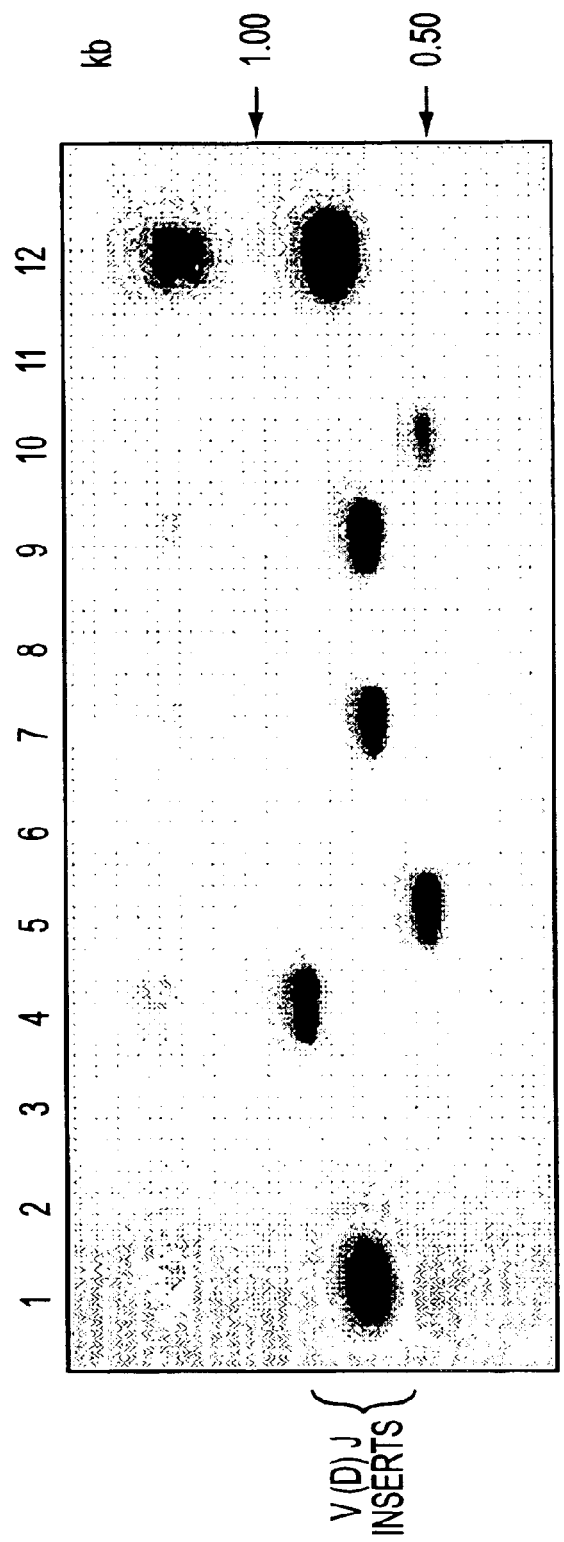

Table 1 describes the oligonucleotides used to detect and clone murine TCR A and B genes. Sequences of oligonucleotides that were used to amplify or detect muring TCR gene segments that were cloned from the murine CD8+CTL, 3A3/3C9. As described below in Example 1, inverse PCR (I-PCR) was conducted with RNA, after conversion to dsDNA and circle formation. TCR gene segments were amplified utilizing CA-S and CA-AS primers as shown in FIG. 2A. These primers amplify a fragment of ~800 bp. The CAM primer was used as shown in FIG. 2B, as a probe to detect TCR A gene fragments amplified utilizing the CA (S+AS) primers. The full-length murine TCR cDNA was amplified from cellular RNA using primers VA16-5' and CA-3' with added restriction sites as shown. Similarly, TCR B cDNAs were cloned utilizing the CB-AS and CB-S primers from the I-PCR generated circles as described below in Example 1. The CBM probe was used to detect TCR B genes utilizing Southern hybridization. The full-length TCR B gene was amplified from cellular RNA using VB-5' and CB-3' primers with added restriction sites as shown. Numbering for all sequences is relative to the initiating ATG codon (+1) of the TCR cDNA sequences.

Table 2 describes antigen presenting cells (APCs) used in studies of TCR specificity. Cell lines as shown were used in the study as targets either by peptide sensitization (T2 cells), or after transfection of mutant p53 (Saos/p53) compared to the parental p53 cell line (Saos). The remaining cell lines are positive for p53 expression as detected by immunohistochemistry, and differ in their expression of the HLA A*0201 antigen. HLA A*0201 expression was determined by immunofluorescence as described (Yu et al, supra). p53 expression as determined by immunohistochemistry was graded on a scale of 0 to 4+ based on the intensity of staining of the majority (>75%) of cells.

Table 3 describes the deduced amino acid sequence of gene segments and their junctions for TCR A and B cDNA from p53 specific CTL clone 3A3/3C9. The TCR gene sequences were determined as described below, after sequence analysis of the complete mu cDNA. The nucleotide sequence was translated and the corresponding open reading frame for the TCR amino acid sequence was determined. Identification of gene segments that correspond to the variable region (AV16), junctional region (AJTA13) are shown, as well as the amino terminus of the AC protein region. Correspondingly, the gene segments for the TCR B cDNA are identified for the varaiable region (VB8.1), diversity region (BD2), junctional region (BJ2.6), and the constant region gene used for this cDNA (BC2).

DETAILED DESCRIPTION OF THE INVENTION

The present invention is directed to cloning the mRNAs encoding the predominantly expressed TCR sequences from a mu CTL clone derived from immunized transgenic (Tg) mice which recognizes endogenously processed hu p53 restricted by HLA A*0201. The invention is also directed to the use of the cloned DNA to transfect human T-cells to produce cytotoxic T-cells, especially CD8$^+$ cytotoxic T lymphocytes which express the p53-specific T-cell receptor (TCR). The invention is further directed to a method for treating an individual having a tumor that overexpresses p53 and is HLA A*0201$^+$.

The present invention relates generally to the field of immunology. Various terms and methods can be found in the leading texts and immunology publications. One important text is William Paul's Fundamental Immunology, Third Edition Raven Press Ltd: New York (1993), which is incorporated herein by reference in its entirety. Other useful texts include Hood et al., Immunology, Second Ed., Benjamin/Cummings: Menlo Park, Calif. (1984), Current Protocols in Immunology, Volumes I–III, Coligan, J. E., ed. (1994), Manual of Clinical Laboratory Immunology, Third Edition, N. R. Rose et al., American Society for Microbiology (1986), each of which is incorporated herein by reference.

Molecular genetics has shown that mutations in the p53 gene, which are generally single base missense mutations (Levine et al., *Nature*, 351:453–456, 1991; Hollstein et al., *Science*, 253:49–53, 1991), contribute to the development of up to 50% of all cancers (Kovach et al., supra), and often correlate with a greater extent of disease and a worse outcome (Chang et al., *J. Clin. Oncol.*, 13:1009–1022, 1995) Mutations of p53, which nullify its function as a suppresser of cell division (Finlay et al., supra; Eliyahu et al., *Proc Natl Acad Sci USA*, 86:8763–8767, 1989), are associated with a much higher nuclear and cytoplasmic concentration of the p53 protein (Finlay et al., supra). What makes the p53 gene product such an attractive target for an adaptive immune response is that the intracellular concentration of nonmutated p53 is normally very low (Zambetti et al., supra; Reich et al., *Nature*, 308:199–201, 1993), and cells expressing normal p53 at low levels would most likely escape an enhanced immune response to over-expressed mutant p53.

There are reports describing isolation of CTL using in vitro stimulation with HLA restricted peptide motifs from p53 and from hu peripheral blood with HLA A*0201 binding peptides of p53 (Ropke et al., *Scand. J. Immunol.*, 42: 98–103, 1995; Houbiers et al., *Eur. J. Immunol.*, 23:2072–2077, 1993). In fact, the precursor frequency for p53 wt epitope specific CTL in normal volunteer peripheral blood is as high as 1:27,000 Ropke et al., supra). Yet, it is difficult to generate p53 peptide-specific CTL from hu peripheral blood which are capable of killing p53 expressing tumor cells (Nijman et al., *J. Immunotherap.*, 14: 121–126, 1993. In fact, there are only limited reports describing hu CTL clone that recognize endogenously processed p53, and these only recognize a small subset of p53 over-expressing hu tumors (Ropke et al., *Proc Natl Acad Sci USA*, 93:14703–14707, 1996; Chikamatsu et al., *Clin. Cancer Res.* 5:1281–1288, 1999). Taken together, this data points to either thymic or peripheral tolerance as the cause of the deletion or inactivation of hu CTL with high enough affinity to kill tumor cells which over-express endogenous p53. There is substantial evidence that p53 is expressed throughout development, suggesting that it may play a role in neonatal thymic deletion of p53-specific T cells (Schmid et al., *Development*, 113:857–865, 1991). Therefore, it is unlikely that a direct immunization approach in cancer patients utilizing p53 sequences, either peptides or DNA will stimulate a high affinity immune response if the appropriate T cells are deleted or non-functional. By contrast, appropriately immunized mice generate a vigorous response to both mutant and non-mutant hu p53 epitopes.

Adapting the vigorous immune response of mouse CTL to hu CTL would need to occur in order to exploit p53 recognition to benefit cancer patients. This can be accomplished by transferring immunoglobulin or TCR specificity to hu T cells. Several groups have been investigating an approach involving the generation and transfer of chimeric T cell receptors consisting of monoclonal antibody single-chain Fv linked to the intracellular signaling domain of CD3ζ or FcγRIII (Goverman et al., *Cell*, 60:929–939, 1990). By transferring chimeric receptors to mu or hu effector cells it has been possible to generate CTL with antibody specificity, which secrete cytokine and mediate lysis of appropriate antigen presenting cells. The ability of these modified cells to mediate tumor rejection in in vivo models has been more difficult to demonstrate (Hekele et al., *Int. J. Cancer*, 68:232–238, 1996). This may result from the relatively high affinity immunoglobulin/antigen interaction, and a resulting inadequate recycling mechanism between single CTL and multiple tumor cells. In addition, CTL with immunoglobulin specificity may lack the ability to recognize intracellularly processed antigens presented in the peptide binding groove of cell-surface MHC molecules. Such would be the case for p53, which is exclusively expressed intracellularly.

A potent anti-hu p53 CD8+ CTL response develops in HLA A*0201 Tg mice after immunization with peptides corresponding to HLA A*0201 motifs from hu p53. Mice immunized with the hu $p53_{149-157}$ peptide develop a CTL response that is of modestly high affinity, and is capable of recognizing hu tumor cells expressing mutated p53. In accordance with the present invention, DNA encoding the predominantly expressed TCR sequences are molecularly cloned from a mu CTL clone derived from immunized Tg mice which recognized endogenously processed hu p53 restricted by HLA A*0201. The DNA is cloned using conventional techniques, such as the preparation of cDNA from the mRNAs of the predominately expressed TCR sequences from any of the mu CTL clones derived from immunized Tg mice which recognizes endogenously processed hu p53, preferably endogenously processed hu p53 restricted by HLA A*0201. Thus, in one embodiment of the present invention, nucleic acids encoding the predominately expressed TCR sequences are provided. In one aspect of this embodiment, a nucleic acid is provided which encodes the A chain of a hu p53-specific, HLA restricted mu TCR. In a second aspect, a nucleic acid is provided which encodes the A chain of a hu p53-specific, HLA restricted mu TCR. In a third aspect, a nucleic acid is provided which encodes both the A chain and the B chain of a hu p53-specific, HLA restricted mu TCR. In a preferred embodiment, the A chain and B chain are prepared from the mu CTL clone 3A3/3C9. The nucleotide and amino acid sequences of the A chain are set forth in SEQ ID Nos:18 and 19, respectively. The nucleotide and amino acid sequences of the B chain are set forth in SEQ ID Nos:20 and 21, respectively.

The present invention is also directed to nucleic acids which hybridize to the nucleic acids of SEQ ID Nos:18 and 20 under stringent hybridization conditions and which encode proteins having the same function as the proteins of SEQ ID Nos:19 and 21, i.e., creation of a functional TCR. Such hybridization techniques are well known to the skilled artisan. Suitable hybridization conditions are described in Sambrook et al. (*Molecular Cloning: A Laboratory Manual*, 2nd Ed., Cold Spring Harbor Laboratory, Cold Spring Harbor, N.Y., 1989) and Ausubel et al. (*Current Protocols in Molecular Biology*, John Wiley & Sons, New York, 1992). Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at about 65° C. The functionality of an encoded product can be determined by a variety of assay techniques including, for example, any of the techniques described below. Thus, one of the encoded proteins (i.e., the one encoded by a nucleic acid which hybridizes to SEQ ID NO:18) has the same function as chain A of the hu p53-specific, HLA restricted mu TCR and the other encoded protein (i.e., the one encoded by a nucleic acid which hybridizes to SEQ ID NO:20) has the same function as chain B of the hu p53-specific, HLA restricted mu TCR. Consequently, the two encoded proteins will produce a hu p53-specific, HLA restricted mu TCR, preferably a hu p53-specific, HLA A*0201 restricted mu TCR.

The present invention also includes vectors and expression vectors containing the cloned A and/or B chains. In accordance with the invention, a vector or an expression vector refers to a replicable unit (self replicating or capable of replication with a helper vector) of DNA or RNA in a form which is capable of being introduced into a target cell by transformation, electroporation, transduction or viral infection, and which codes for the expression of a heterologous structural coding sequence, for example, the A chain of a hu-p53, HLA restricted mu TCR. In an expression vector, the DNA or RNA is transcribed into MRNA and translated into protein under the control of elements having a regulatory role in gene expression. Such expression vectors will preferably also contain appropriate transcription and translation initiation and termination sequences. That is, the nucleic acids of the present invention are operably linked to transcription control elements. Suitable regulatory elements are well known to skilled artisans. In a further embodiment, the present invention also includes a nucleic acid, for example, the A chain of a hu-p53, HLA restricted mu TCR, operably linked to transcription control elements.

The A chain and B chain TCR nucleic acids, or the nucleic acids which hybridize to such nucleic acids and which encode proteins having the same function as the A chain and the B chain, are transfected in the corresponding $A^-$ and $B^-$ Jurkat-CD3$^-$ mutant T cell lines, and each rescued CD3 surface expression. In a preferred embodiment, the A chain and the B chain TCR nucleic acids are transfected as separate nucleic acids. Both TCR chains are simultaneously introduced into Jurkat-CD3$^+$ cells, and the transfected cells are shown to equivalently express the A and B chains by PCR. Mu A/B TCR transfected Jurkat cells recognized hu T2 cells sensitized with the hu p53$_{149-157}$ CTL epitope, but not T2 cells loaded with a non-specific CTL epitope. The TCR-transfected Jurkat cells also recognized endogenously processed p53 protein transfected into the SAOS hu osteosarcoma cell line, while not responding to the p53$^-$parental SAOS cell line. Breast and pancreatic tumor cell lines which express mutated p53 endogenously are recognized only if they also expressed HLA A*0201. Normal hu fibroblasts established from skin cultures were not recognized. These results represent the first time that a p53-specific TCR capable of recognizing hu cancer cells was heterologously expressed in a naive recipient cell, converting that cell to one recognizing hu tumor cells with mutated p53.

The functional expression of the mu TCR transfectants succeeded in the presence of CD28 costimulation, which provides a powerful activation stimulus for Th cell function (Hara et al., *J. J. Exp. Med.*, 161:1513–1524, 1985; Guinan et al., *Blood*, 84:3261–3282, 1994; Nunes et al., *Int. Immunol.*, 5:311–315, 1993). Thus, this TCR is useful for combatting human cancer by an adoptive immunotherapy approach which utilizes the strong xeno-recognition of a hu p53 CTL epitope in mouse. Thus, in one embodiment, the present invention is directed to the immunotherapeutic treatment of tumors that over-express p53, and preferably the treatment of tumors that over-express p53 and that are HLA A*0201$^+$.

Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category. Currently, most adoptive immunotherapies are autolymphocyte therapies (ALT) directed to treatments using the patient's own immune cells. These therapies involve processing the patient's own lymphocytes to either enhance the immune cell mediated response or to recognize specific antigens or foreign substances in the body, including the cancer cells. The treatments are accomplished by removing the patient's lymphocytes and exposing these cells in vitro to biologics and drugs to activate the immune function of the cells. Once the autologous cells are activated, these ex vivo activated cells are reinfused into the patient to enhance the immune system to treat various forms of cancer that over-express p53, and preferably the treatment of tumors that over-express p53 and that are HLA A*0201$^+$.

The present invention can be used to treat tumors that over-express p53 in an individual, and preferably to treat of tumors that over-express p53 and that are HLA A*0201+ in an individual. In treating tumors in an individual, it is not required that the cell(s) that is administered to the individual be derived from that individual. Thus, the T lymphocyes can be obtained from a matched donor, or from a culture of cells grown in vitro. Methods for matching haplotypes are known in the art. However, it is preferred that the T lymphocytes be derived from the individual, although such T lymphocytes can also be expanded by culturing in vitro.

It is preferable that treatment continues as long as the tumor regresses. In treating an individual with the T lymphocytes produced according to the invention, the optimal dosage of the cells depends on factors such as the weight of the individual and the severity of the cancer. Generally, a dosage of $10^5$ to $10^{10}$ cells/kg body weight should be administered in a pharmaceutically acceptable excipient to the individual. The cells can be administered by using infusion techniques that are commonly used in cancer therapy (see, e.g., Rosenberg et al., *New Eng. J. of Med.*, 319:1676, 1988). For example, The CTLs of the present invention can be administered to an individual in a CTL-based method of therapy (see, e.g., WO 92/04462). In one embodiment, the CTLs produced in accordance with the present invention can be administered in a pharmaceutically acceptable excipient to a an individual by employing conventional infusion methods (see, e.g., Rosenberg et al., supra). Typically, $10^9$ to $10^{10}$ cells are administered over the course of 30 minutes, with treatment repeated as necessary. The CTLsmay be autologous or heterologous to the individual undergoing therapy. If desired, the treatment may also include administration of mitogens (e.g., phytohemagglutinin) or lymphokines (e.g., IL-2 or IL-4) to enhance CTL proliferation. The optimal dosage and treatment regime for a particular individual can readily be determined by one skilled in the art of medicine by monitoring the individual for signs of disease and adjusting the treatment accordingly.

According to another embodiment of the present invention, the cytotoxic T lymphocytes obtained by the invention can be subjected to successive cultivations. As a result of the cultivation, a culture mixture containing cytotoxic T lymphocytes expanded by a monolayer culture can be obtained. The cytotoxic T lymphocytes separated from the culture mixture are particularly suitable for all kinds of clinical treatments of tumors including adoptive immunotherapies and for tumor researches. Separation and recovery of the expanded CTLs may be conducted according to methods well known to those skilled in the art. For example, pharmaceutical compositions comprising the resulting cytotoxic T lymphocytes as active ingredients may be manufactured by processes well known to those skilled in the art, which may be administered, e.g. injected to the patients from whom the tumor tissues are derived.

The effect of immunotherapy with the CTLs of the present invention on development and progression of neoplastic diseases can be monitored by any methods known to one skilled in the art, including but not limited to measuring: a) delayed hypersensitivity as an assessment of cellular immunity; b) activity of cytolytic T-lymphocytes in vitro; c) levels of tumor specific antigens; d) changes in the morphology of tumors using techniques such as a computed tomographic (CT) scan; e) changes in levels of putative biomarkers of risk for a particular cancer in individuals at high risk; and f) changes in the morphology of tumors using a sonogram.

The practice of the present invention employs, unless otherwise indicated, conventional techniques of chemistry, molecular biology, microbiology, recombinant DNA, cell biology and cell culture, which are within the skill of the art. See, e.g., Maniatis et al. (*Molecular Cloning: A Laboratory Manual*, Cold Spring Harbor Laboratory, Cold Spring Harbor, N.Y., 1982); Sambrook et al. (*Molecular Cloning: A Laboratory Manual*, 2nd Ed., Cold Spring Harbor Laboratory, Cold Spring Harbor, N.Y., 1989); Ausubel et al. (*Current Protocols in Molecular Biology*, (John Wiley & Sons, New York, 1992); Glover (*DNA Cloning*, I and II, Oxford Press, Oxford, 1985); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal (*A Practical Guide To Molecular Cloning*, 1984); the treatise, *Methods In Enzymology* (Academic Press, Inc., N.Y.); *Gene Transfer Vectors For Mammalian Cells* (J. H. Miller and M. P. Calos eds., Cold Spring Harbor Laboratory, Cold Spring Harbor, N.Y., 1987); Harlow and Lane (*Antibodies: A Laboratory Manual*, Cold Spring Harbor laboratory, Cold Spring Harbor, N.Y., 1988); *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); Riott, (*Essential Immunology*, 6th Edition, Blackwell Scientific Publications, Oxford, 1988).

EXAMPLES

The present invention is further described with reference to the following examples, which are offered by way of illustration and is not intended to limit the invention in any manner. Standard techniques well known in the art or the techniques specifically described therein were utilized.

Example 1

Materials and Methods

Cell Lines

Previously described cell lines used in these experiments included

T2 (Salter et al., *EMBO J.*, 5:943–949, 1986),

Saos (Fogh et al., *J. Natl. Cancer Inst.*, 59:21–226, 1977),

Panc-1 (Lieber et al., *Int. J. Cancer*, 15:741–747, 1975),

AsPC-1 (Chen et al., *In Vitro*, 18:24–34, 1982),

MDA-MB231 (Cailleau et al., *J. Natl. Cancer Inst.*, 53:661–674, 1974),

SK-BR3 (Fogh et al., *J. Natl. Cancer Inst.*, 58:209–214, 1977),

Jurkat (Weiss et al., *J. Immunol.*, 133:123–128, 1984), and JRT.3T.1 and J.RT3–3.5 (Weiss, et al., *J. Exp. Med.*, 160:1284–1299, 1984).

The cell lines were obtained from the American Type Culture Collection. The HLA status of each antigen-presenting cell line was determined by polymerase chain reaction (PCR) on genomic DNA as well as by indirect immunoflourescence (IF) as described (Yu et al., supra). p53 expression in these cell lines was confirmed by immunohistochemistry (Table 2) as described (Pileri et al., *J. Pathol.*, 183:116–123, 1977). Briefly, cell lines were pelleted, mixed with agarose gel, fixed in 10% buffered formalin, and embedded in paraffin oil. Cell blocks sections were cut to 5-$\mu$m thickness, mounted on Probe-on slides (Ventanna Biotech System, Tuscon, Ariz.), and baked at 42° C. overnight and then for 1 h at 56° C. The slides were deparaffinized in xylene and hydrated in distilled water. Antigen retrieval was by steaming (Black & Decker Handy Steamer Plus, Hampstead, Md.) with 0.01 M EDTA-Tris buffer (pH 8.0) for 20 min. followed by cooling for 20 min. and rinsing in distilled water (Id.) Slides were stained using a Biotech Techmate 1000 Immunostainer (Ventanna Biotech System). Sections were incubated for 25 min with a 1:1000, 1:2500, and 1:5000 dilution of the D07 mAb specific for hu p53 (NovoCastra Laboratories, Newcastle, England). Sections incubated with PBS served as negative control. Controls were embedded in the same blocks as the tumor tissue. The antibody-antigen complex was detected by a modified ABC method (Ventanna Biotech System), per the manufacturer's directions, with the chromagen 3',3-diaminobenzidine to develop a brown color. The slides were graded by an individual blinded to the sample notation, using a scale of 0 to 4+, based on the intensity of staining of the majority (>75%) of cells. Cells with no staining were graded as 0, and cells with maximal staining with respect to a laboratory control were graded as 4+.

HLA A*0201$^+$ fibroblast cell lines were a kind gift of S. J. Forman (City of Hope). All hu cell lines were maintained in RPMI (supplemented with 10% heat inactivated fetal bovine serum, 100 units/ml penicillin, 100 $\mu$g/ml streptomycin, and fresh glutamine). Saos-p53 was derived from transfection of the p53 deficient parent cell line with mutated p53 (r to h at position 175) as previously described (Yu et al., supra).

Derivation of mu huP53-specific CTL Clone p53 specific CTL clones were generated by immunizing HLA A*0201 Tg mice (a kind gift of V. H. Engelhard, University of Virginia) with the immunodominant hu p53$_{149-157}$ CTL epitope and the PADRE (Alexander et al., *Immunity*, 1:751–761, 1994):Th peptide emulsified in incomplete Freund's adjuvant (IFA) as described (Yu et al., supra). Spleen cells suspensions were prepared from immunized animals, and further stimulated with syngeneic lipopolysaccharide treated splenic blasts and loaded with the priming peptide as described (Wentworth et al., *Mol. Immunol.* 32:603–612, 1995). Additional in vitro stimulations (IVSs) were performed every seven days using citric acid treated and peptide pulsed Jurkat T cells transfected with HLA A*0201 as antigen presenting cells (APCS) (Yu et al., supra). Long term CTL lines were established by restimulating peptide primed CTLs at weekly intervals with the addition of RAT T-stim with Con A (Collaborative Biomedical Products, Bedford, Mass.). After three rounds of IVS, p53$_{149-157}$-reactive CTL lines were cloned by limiting dilution in 96-well flat-bottomed micro titer plates. The cells were plated under IVS conditions as described above, and were re-fed seven days later with identical fresh medium.

Two to three weeks later, clones were expanded by restimulation in 24-well plates. Several clones were evaluated for recognition of p53 sensitized T2 cells and were further expanded for additional studies, including the demonstration of recognition of endogenously processed p53 on transfected cells and tumor cell lines. Several of the clones exhibited equivalent cytotoxicity, and were further evaluated for TCR usage.

Chromium Release Assay Using mu CTL 3A3/3C9

To assess peptide specific lysis, T2 cells were labeled with 150 uCi (ICN, Costa Mesa, Calif.) $^{51}$Cr and peptide pulsed (1.0 μM) for 90 minutes. For cytotoxic assays involving cell lines without peptide sensitization, cells were pretreated for 24 hours with 20 ng/ml hu IFN-γ and 3 ng/ml hu TNF-α and labeled with $^{51}$Cr for 90 minutes. Labeled target cells and diluted effector cells were coincubated for 4 hours. Supernatants were harvested (Skatron Instruments, Norway) and counted using a gamma counter (Packard Instrument Company, Meriden, Conn.). Specific lysis was determined as follows: % specific release=[(experimental release–spontaneous release)/(maximum release–spontaneous release)]×100.

Cloning and Characterization of A/B TCR cDNAs Using RT-PCR and Inverse-PCR mu p53$_{149-157}$-specific CTL Clone 3A3/3C9 was grown after stimulation with mAb 2C11 without feeder cells. RNA was prepared using a modification of the method of Chomczynski and Sacchi (Chomczynski et al., *Anal. Biochem.*, 162:156–159, 1987) using the Trizol reagent (Life Technologies, Gaithersburg, Md.). One μg of total RNA was then annealed to 20 ng of oligo (dT)$_{12-18}$ (Pharmacia, Uppsala, Sweden) at 65° C. for 10 minutes. The first-strand cDNA was synthesized in a 20 μl volume using 5 units of avian myeloblastosis virus (AMV) reverse transcriptase (RT) at 45° C. for 60 minutes. The second-strand of the cDNA was synthesized by addition of 15 units *Escherichia coli* DNA ligase, 18 units of *E. coli* DNA polymerase, and 1.75 units of *E. coli* RNase H (New England Biolabs, Beverley, Mass.) according to the manufacturer's recommendations. After incubation for 120 minutes at 16° C., 1 unit of T4 DNA polymerase was added for blunt end formation. The double-stranded cDNA (dsDNA) was circularized by incubation with 1 unit of T4 DNA ligase (Life Technologies). TCR cDNA fragments were amplified from the circles using PCR with Taq DNA polymerase and the recommended buffer (Perkin Elmer Corp., Norwalk, Conn.) for 35 cycles using the GeneAmp 9600 (Perkin Elmer Corp., Norwalk, Conn.). The amplification cycle consisted of denaturation at 94° C. for 30 seconds, annealing at 53° C. for 30 seconds and extension at 72° C. for 30 seconds. Primers used for one inverse PCR were CA-antisense (SEQ ID NO:1) and CA-sense (SEQ ID NO:2). Primers used for the second inverse PCR were Cβ-antisense (SEQ ID NO:6) and Cβ-antisense (SEQ ID NO:7) (Table 1). Fifteen picomoles of each primer was added to the reaction. The products of the PCR reaction were separated on a 1% agarose gel, and DNA fragments of the expected sizes were removed from the gels and purified with the help of glass beads (GeneClean II; BIO 101, La Jolla, Calif.). The DNA fragments were cloned into the pGEM-T vector (Promega, Madison, Wis.). Resultant recombinants were screened by Southern blot hybridization analysis using TCR-specific primers CAM (SEQ ID NO:3) and CBM (SEQ ID NO:8) (Table 1). DNA sequencing was carried out on 5–10 candidate TCR A or B genes with complementary primers for the Sp6 or T7 promoter sites flanking the cloning sites.

Reamplification by reverse transcription of cellular RNA utilizing a combination of specific sense V gene segments from the identified VA or VB genes (Table 1) (VA16, Seq. ID 4 or VB8, Seq. ID 9) from the previously identified V genes along with either CA 3' (SEQ ID NO:5) or CB3'(SEQ ID NO:10antisense primers (Table 1) were used to make mu A and B cDNA fragments into full length genes. Recovered PCR DNA fragments were then digested with XbaI and SalI restriction endonucleases for cloning into expression vectors. The whole cDNA for each gene was resequenced, and examples were found without PCR-induced errors. Both A and B TCR cDNAs were subcloned separately into the expression vector, pCI-neo (Promega) containing the neomycin phosphotransferase gene.

TABLE 1

Oligonucleotides used to detect and clone murine TCR A and B genes.

| Primer Name | | Nucleotide Location |
|---|---|---|
| TCR A Sequence (Seq. ID No.) | | |
| CA-AS | CATAGCTTTCATGTCCAGCACAG (1) | 570–548 |
| CA-S | CTCCTGCTACTGTGTGTATTGAGC (2) | 1259–1282 |
| CAM | GTGCTGTCCTGAGACCGAGGATC (3) | 467–445 |
| VA16-5'(XbaI) | TCTCTAGACCATGCTGATTCTAAGCCT (4) | −10 to 17 |
| CA-3'(SalI) | TGGTCGACTCAACTGGACCACAG (5) | 827–805 |
| TCR B Sequence (Seq. ID No.) | | |
| CB-AS | GACCTCCTTGCCATTCAC (6) | 542–526 |
| CB-S | ACCATCCTCATGAGATCC (7) | 811–829 |
| CB-M | GACCTTGGGTGGAGTCACATTTCTCAGATC (8) | 420–391 |
| VB8-5'(XbaI) | ACTCTAGATGGGCTCCAGACTC (9) | −7 to 15 |
| CB-3'(SalI) | CAGTCGACATAAAAGTTTGTCTCAGG (10) | 937–912 |

Transfection of A and B TCR cDNAs into Jurkat CD3$^+$/$^-$T Cells

The mu TCR A chain was introduced into the JRT-T3.1 cell line that lacks the TCR A chain under the selective control of the antibiotic G418. Similarly, the mu TCR B cDNA was introduced into JRT-T3.5 cell line that lacks TCR B chain. Both TCR A and B chain cDNAs were introduced into the Jurkat T cell positive for both TCR A/B genes under the selective control of the antibiotic G-418. This approach was taken based upon previous work, showing more balanced expression of both TCR chains in non-TCR mutant cell lines (Zambetti et al., supra).

Gene transfer was accomplished through the use of standard liposome transfection procedures (Lipofectin, Life Technologies). Briefly $2 \times 10^6$ cells were resuspended in 0.8 ml serum-free growth medium and put into one well of a six-well plate. 0.2 ml of the Lipofectin Reagent-DNA complexes containing 5 μg plasmid DNA and 20 μl Lipofectin were added to the cell suspensions with gentle mixing. The cultures were then incubated at 37° C. in a 5% $CO_2$ incubator for 5 hours and 4 ml growth medium supplemented with 10% FCS was added. After two days, the selective antibiotic was added. The media was changed weekly until resistant cells grew to adequate numbers. Transfectants were cloned by limiting dilution at 0.3 cell per well in 96 well flat bottomed plates. Positive colonies were scored when there was substantial growth, usually after two weeks. Colonies were expanded into successively larger flasks, and when there were enough cells, further analysis was performed.

Flow Cytometry Analysis of mu TCR Chains Transfected into Jurkat-CD3+ and Jurkat-CD3− Cells TCR mutants JRT T3.1 and J.RT3-T3.5 do not express a cell-surface TCR because they lack expression of either TCR A or B chains; as a consequence, they are both negative for surface CD3 (Saito et al., *J. Immunol.*, 139:625–628, 1987). Transfection of TCR A or B chain genes, restores surface expression of CD3 as detected by monoclonal antibody OKT3 (Id.). Previous work showed that a combination of hu and mu TCR chains could rescue surface CD3 expression on Jurkat mutant cells (Saito et al., *Nature*, 329: 256–259, 1987. The transfectants were examined by flow cytometry after staining with mAb OKT3 and a FITC secondary antibody. In addition, the mu VB8-specific mAb F23.1 (Staerz et al., *J. Immunol.*, 134:3994–4000, 1985) was utilized to detect surface expression of the mu p53-specific CTL clone TCR B chain gene. Matched isotype controls were used in each experiment for background fluorescence. Events (10,000) were collected for each histogram on the MOFLO flow cytometer (Cytomation Instruments).

RT-PCR Analysis of mu TCR RNA in Jurkat Transfectants

Molecular analysis of the expression of the transfectant RNA in JRT.3T.1 and J.RT3-T3.5 cells was performed by standard RT PCR method (Casanova et al., *J. Exp. Med.*, 174:1371–1383, 1991). mu specific TCR primers (VA or VB and CA or CB) were used to amplify either the TCR A or B genes in the respective transfectants (Table 1). In the doubly transfected Jurkat cell, both mu A and B TCR chains were amplified at the same time, to examine the equivalence of expression in various transfectant cell lines.

Proliferation Assays Using Jurkat mu TCR Transfectants

For recognition of p53 epitope, T2 cells (APC) were preincubated with 50 μM peptide for 4 hours. Then, $1 \times 10^5$ cells per well in a 96-well round-bottomed plate were incubated with $1 \times 10^5$ Jurkat transfectants at 37° C. in a 5% $CO_2$ incubator. For recognition of endogenously processed hu p53 by TCR transfectants, $1 \times 10^5$ transfected cells were incubated in the presence of a mAb recognizing CD28 (mAb9.3) (Saito et al., supra) with $1 \times 10^5$ HLA A*0201-positive or HLA A*0201-negative tumor cells or fibroblasts pretreated with 20 ng/ml interferon-γ (IFN-γ) and 3 ng/ml tumor necrosis factor-α (TNF-α) at 37° C. in a 5% $CO_2$ incubator. The medium was harvested after 24 hours and interleukin 2 (IL-2) production was assessed in a bioassay using an IL-2-dependent cell line (CTLL) (Gillis et al., *Nature*, 268:154–156, 1977). Briefly, triplicates of $5 \times 10^3$ CTLL per well in a 96-well flat-bottomed plate were incubated with 50 μl of recombinant IL-2 standard or medium at 37° C. in a 5% $CO_2$ incubator for 24 hours. The cultures were harvested after 4 hours after pulsing with 1 μCi [$^3$H]-thymidine. [$^3$H]-thymidine incorporation was measured by liquid scintillation counting. All results are expressed as the mean of triplicate counts per minute (cpm).

Example 2

Figure 1:
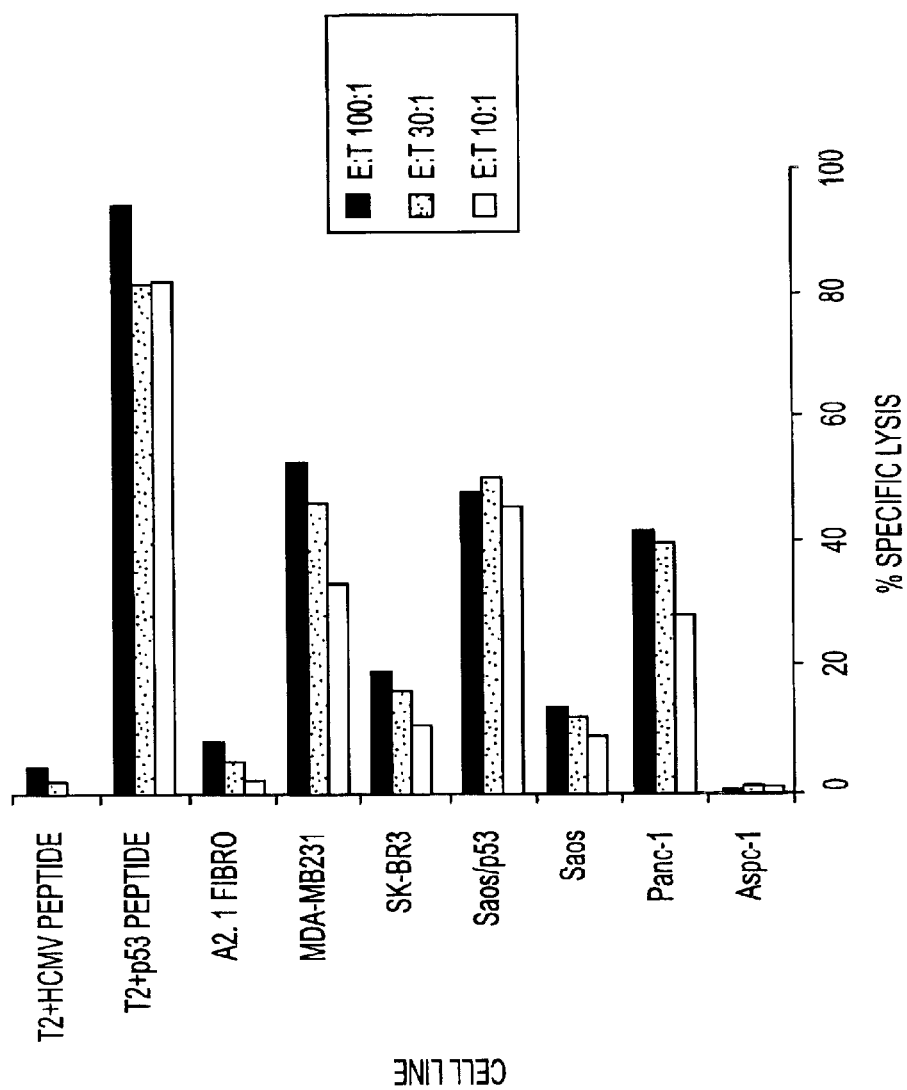
FIG. 1 shows cytotoxic activity of anti-$p53_{149-157}$-CTL effector cells using hu cell line targets in a 4-hour chromium release assay (CRA). E:T ratios were 100:1, 30:1 and 10:1. The following cell lines were used as targets: T2 pulsed with a $pp65_{495-503}$ epitope (T2+HCMV peptide), T2 pulsed with $p53_{149-157}$ epitope (T2+p53 peptide), HLA A*0201 fibroblasts, breast cancer cell lines MDA-MB231 and SK-BR3, osteosarcoma line Saos/p53 transfected and native cells, and pancreatic cancer cell lines Panc-1 and AsPC-1. SEs of triplicate cultures was always <5% of the mean.

Mu CTL From HLA A*0201 Tg Mice Specifically Recognized p53+/HLA A*0201-Expressing Hu Cells It had previously been shown that immunization of HLA A*0201 Tg mice in the C57 BL/6 background with $p53_{149-157}$ resulted in the generation of HLA A*0201 restricted CTLs, which could cause the recognition and lysis of adoptively transferred hu tumor cells in SCID mice (McCarty et al., supra). One of these clones (3A3/3C9) was further examined for the strength of its recognition of the hu $p53_{149-157}$ HLA A*0201-restricted epitope using a CRA. It was reconfirmed that the hu TAP transporter mutant cell line T2, when loaded with the $p53_{149-157}$ CTL epitope, was well recognized at all E:T ratios examined (FIG. 1). This recognition was specific, because an HLA A*0201 binding, CMV-pp65 CTL epitope (Diamond et al., *Blood*, 90:1751–1767, 1997) is not recognized by this clone in in vitro assays. Clone 3A3/3C9 was further evaluated for its specificity of recognition of hu tumor. APC used are described in Table 2, and reflect examples of hu fibroblasts or tumors expressing p53, or HLA A*0201, or both, or neither. CTL clone 3A3/3C9 at varying E:T ratios was incubated with a series of hu tumors, and the results shown in FIG. 1 were obtained. Cell lines that were not HLA A*0201+ (ASPC-1 and SKBR3) were not efficiently lysed. Cell lines which did not express hu mutant p53 (SAOS; A2.1 Fibro), were not lysed unless pulsed with the $p53_{149-157}$ peptide. Tumor lines that were HLA A*0201+ and p53+ were efficiently lysed by the mu CTLs (PANC-1, SAOS/p53, and MDA-MB231). The recognition properties of the mu CTL clone demonstrates that it is able to distinguish between hu tumors, which express the appropriate HLA type and mutant overexpressed forms of p53, from those that do not express both molecules. (Table 2)

TABLE 2

| APCs used in studies of TCR specificity | | | |
|---|---|---|---|
| Cell Lines | Cell Type | HLA-A*0201 Expression | p53 Accumulation |
| T2 | B and T lymphoblast hybrid | + | − |
| Saos | Osteosarcoma | + | − |
| Saos/p53 | Osteosarcoma | + | ++++ |
| AsPC-1 | Pancreatic adenocarcinoma | − | − |
| Panc-1 | Pancreatic adenocarcinoma | + | ++++ |
| SK-BR-3 | Breast Carcinoma | − | ++++ |
| MDA-MB-231 | Breast Carcinoma | + | ++++ |

The amount of p53 overexpression required for recognition is difficult to quantify. Cells containing wt p53 are generally negative by immunohistochemistry and are not recognized (Table 2). In contrast, all of the cell lines which have been examined with mutated p53 stain intensely for p53 immunohistochemistry and are recognized (Yu et al., supra; McCarty et al., *Ann. Surg. Oncol.*, 5: 93–99, 1998; Peralta et al.,*J. Urol.*, 162:1806–1811, 1999). It is likely that the mu CTLs recognize the wt form of the p53$_{149-157}$ epitope, because the mutations in these cell lines are known to be at a different location of the p53 DNA sequence (Yu et al., supra). Overexpression of p53, caused by specific mutations outside the p53$_{149-157}$ epitope location, is essential for recognition of the mu CTL 3A3/3C9. Because this clone was used earlier in in vivo experiments, which demonstrated that the particular TCR was capable of rejecting hu tumors in a mu SCID model, the data for both in vivo and in vitro studies confirmed the appropriateness of using this TCR for gene transfer studies (McCarty et al., *Cancer Research, supra*).

Example 3

Molecular Cloning of Hu p53-Specific TCR

Using a novel technique of molecular cloning referred to as "Inverse PCR"(Inaba et al., *Int. Immunol.* 3:1053–1057, 1991; Uematsu, *Immunogenetics*, 34:174–178, 1991), without the formal use of DNA libraries, the TCR A and B chain cDNAs were identified (FIG. 2). In FIG. 2A, the method referred to as inverse PCR shows how the RNA from the CD8$^+$ CTLs was converted to circular dsDNA and subsequently amplified using conventional PCR into linear molecules containing specific TCR sequences. TCR-specific primers derived from the constant region of either the TCR A or B genes, were used in amplifying TCR-specific cDNA into amounts that could easily be subcloned into standard plasmid vectors. This amplification step increased the number of TCR-specific colonies after transfer to bacterial plates. Single colonies were picked, minipreps were made, and the size of inserts was examined using agarose gels, and then transferred to nylon membranes. Inserts >0.7 kb will contain sequence from VA-JA and CA or VB-DB-JB and CB DNA segments. The nylon membranes were hybridized with oligonucleotides derived from the CB region (Table 1), and those inserts that are TCR-specific were visualized using $^{32}$P radioactivity after end-labeling (FIG. 2B). Colonies that contained inserts >0.7 kb were then sequenced in their entirety to identify the usage of particular VB-DB-JB segments (Table 3). Similar methodology was used to identify and sequence the CA and VA-JA segments.

TABLE 3

Deduced Amino Acid Sequence (SEQ ID NO:) of Gene Segments and Their Junctions for TCR A and B cDNA from P53-specific CTL Clone 3a3/3c9

|       | AV1 6            |       | AJTA13                       | AC                    |
|-------|------------------|-------|------------------------------|------------------------|
| TCR A | VYFCAMR (11)     |       | DTNAYKVIFGKGTHLHVLP (12)     | NIQNPEP (13)           |
|       | BV8.1            | BD2   | BJ2.6                        | BC2                    |
| TCR B | AVYFCASS (14)    | PSS (15) | YEQYFGPGIRLTVL (16)       | EDLRNVTPP (17)         |

The criterion for selection of a TCR cDNA sequence as being the correct RNA transcript corresponding to the expressed form of the receptor from the CD8$^+$ T cell clone is its frequency of usage. After cloning of individual TCR transcripts in plasmid vectors, it is still important to test whether the predominantly expressed transcript represented the expressed RNA transcript from the original T cell clone. Sequence analysis of inserts from plasmids revealed that five of seven candidate TCR cDNAs had the identical sequence, whereas two differed from the other five and from each other. Presumably, the two non-identical sequences arose from residual contaminating feeder cells. The clonal TCR A and B cDNAs were identical to the expressed transcript in the original mu CD8$^+$ CTLs was confirmed using RT-PCR. An oligonucleotide primer was derived from the nucleotide sequence of each unique V gene from both clonal TCR A and B cDNAs, together with an antisense primer to the constant gene segment of both A (CA-3') and B (CB-3') TCRs (Table 1). Total cellular RNA was amplified with the oligonucleotide pairs, using RT-PCR, then individual cDNA molecules were molecularly cloned in plasmid vectors as described above in Example 1. The complete cDNAs for both TCR A and B genes were sequenced from five separate plasmid clones. The sequences were aligned and compared, and found to be identical for both the TCR A and B genes. The deduced amino acid sequences at the junctions of gene segments comprising both TCR CDNA chains are shown, and both nucleic acid sequences have been deposited in the EMBL database (Table 3). Subsequently, both TCR A and B cDNAs were transferred to plasmid expression vectors for use in expression studies in eukaryotic cells.

Example 4

Transfection of A and B TCR cDNAs into Jurkat T Cell Lines

Figure 3A:
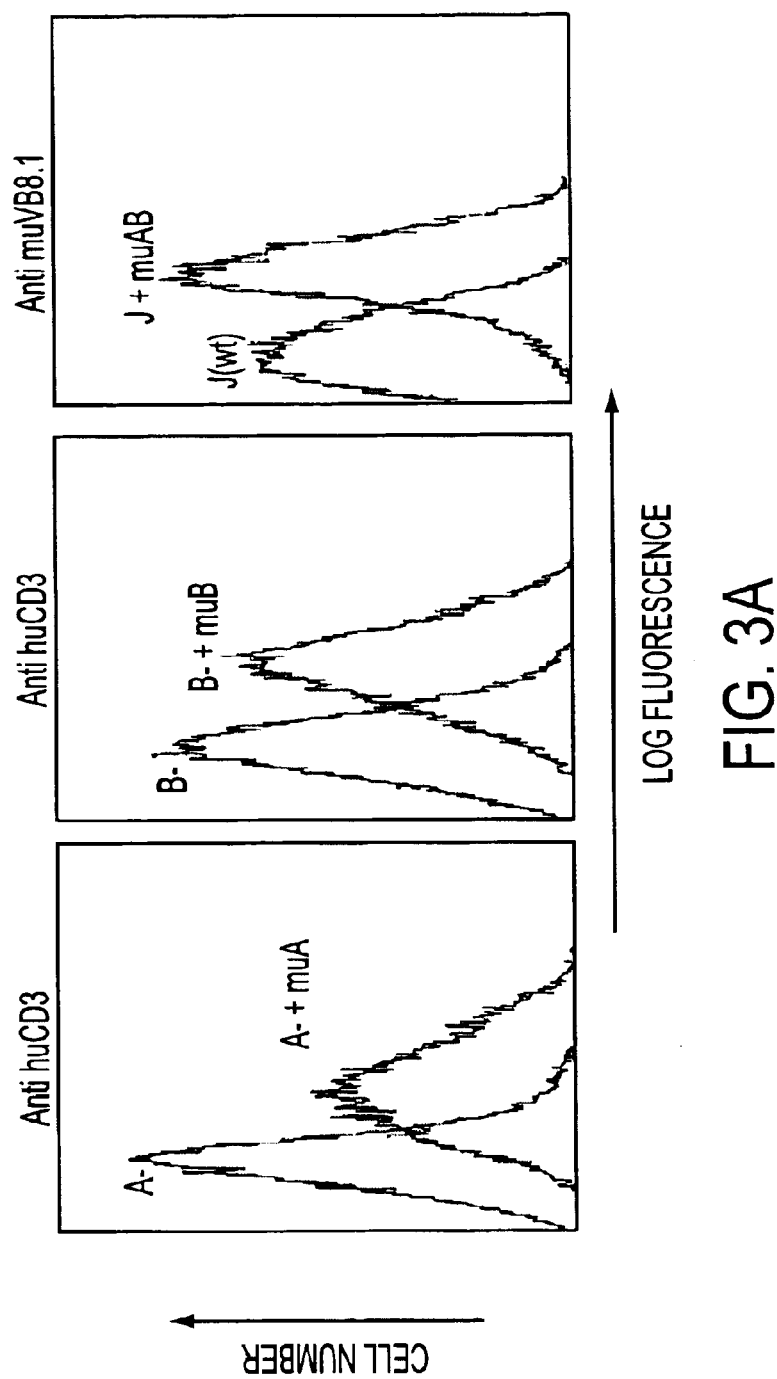
FIGS. 3A and 3B show expression of mu A and B TCR chains in transfected Jurkat cell lines.

Jurkat A or B TCR mutants do not express a TCR:CD3 complex on the cell surface (Saito et al., supra). Earlier investigations showed that in the mutants developed by the Weiss Laboratory, that transfection with cDNA encoding single TCR chains could restore cell surface TCR:CD3 expression (Saito et al., *Nature*, 325:125–130, 1987). It was previously shown that mu TCR subunit cDNAs could restore surface TCR:CD3 expression in similar mutants, as a result of the sequence and functional homology of mu and hu TCR chains. Restored expression of the complex could be detected and quantitated using the mAb OKT3 (Saito et al., *J. Immunol.*, supra). These properties of the mutant-TCR cell lines were utilized to examine the functional expression of the individual muTCR CDNA chains that had been transfected (FIG. 3). The data shown in FIG. 3A, shows that both the mu TCR A or B chain could individually rescue TCR: CD3 expression from the cognate TCR mutant cell line. Since the cell-surface expression of the TCR:CD3 complex depends upon the newly introduced TCR chain, it can be concluded that both the muTCR A and B chains were appropriately expressed. In addition, these were able to integrate into a complex with the endogenous hu chains to form the cell surface form of the TCR:CD3 complex detectable with OKT3 (FIG. 3A).

Since both mu TCR chains were functionally expressed, it prompted us to determine whether they would interact with each other as well as the other hu CD3 chains to form a muTCR: huCD3 complex in the Jurkat T cell mutants. Since it has already been shown that both mu and hu TCR chains can independently assemble into a cell surface TCR:CD3 complex, it was logical to use the mutant Jurkat T cell lines as a host for simultaneous transfection of both muTCR chains. Nonetheless, it was observed that dual transfection of both mu TCR chains, no matter how varied the relative starting concentrations of expression plasmid, ultimately resulted in imbalanced expression of either the mu TCR A or B chain in the respective Jurkat T cell mutant. For this reason, expression and function of the mu TCR A and B chains was examined in wt-Jurkat. The surface expression of the mu TCR B chain was initially assessed in the doubly transfected Jurkat T cell, using the only available mu-TCR specific mAb that would selectively detect the mu TCR chain associated with hu TCR:CD3 complex (FIG. 3A). Cell surface staining with mAb F23.1 did not address the expression level of the mu TCR A chain. However, no good mu mAb is available with which to detect the mu TCR A chain in the TCR:CD3 complex with either mu or hu TCR chains. Furthermore, a mAb, which will detect the mu-specific heterodimer was not available to us, making it difficult to determine whether the mu A/B heterodimer was assembled on the cell surface. Instead, a PCR method was used to simultaneously evaluate the mRNA expression for each of the transfected mu TCR chains.

Example 5

MuTCR mRNA Transcripts are Equally Expressed in Non-Mutant Jurkat T Cell Lines

Figure 3B:
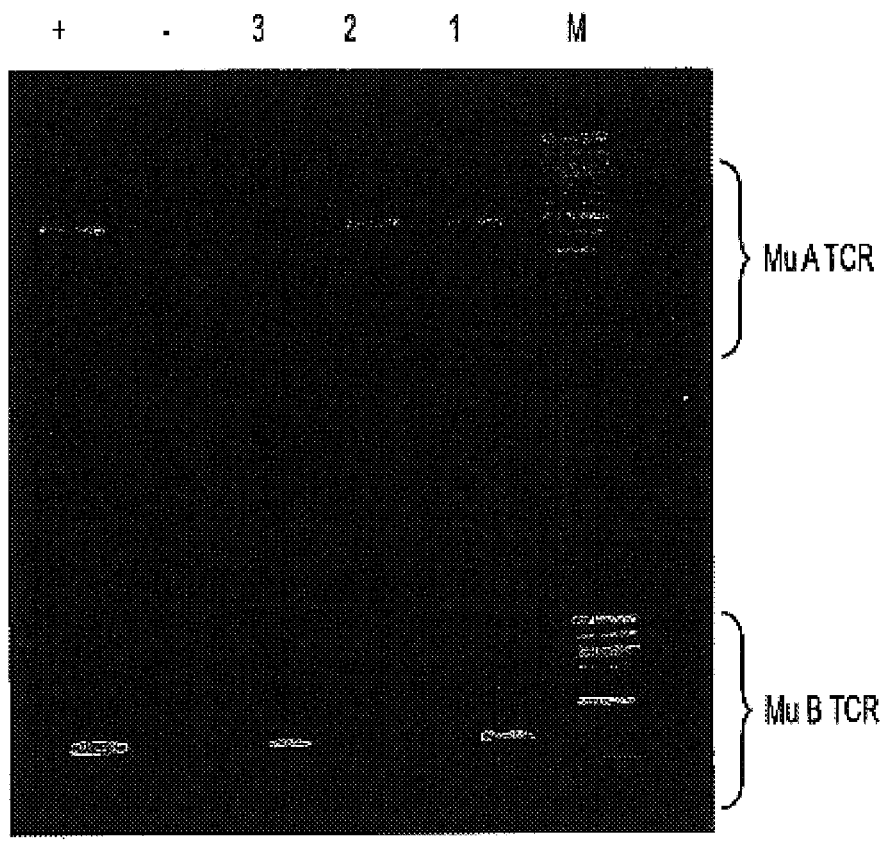

Expression of muTCR transcripts was evaluated by PCR in the double muTCR Jurkat transfectants, as shown in FIG. 3B. The expression of both mu TCR A and B transcripts in wt-Jurkat T cells was examined, it was found that Jurkat clones with imbalanced (FIG. 3b, lanes 2–3) and others with an equivalent level of mu TCR A and B expression (FIG. 3B, lane 1). Several different clones derived from the wt-Jurkat T cell exhibited a balanced expression of the muTCR A and B chains that was stable over a 6-month period. Examples of these T cell transfectant clones were further examined in functional analysis as described below.

Example 6

Functional Activation of IL-2 Expression in Mu-TCR Jurkat Transfectants

Figure 4A:
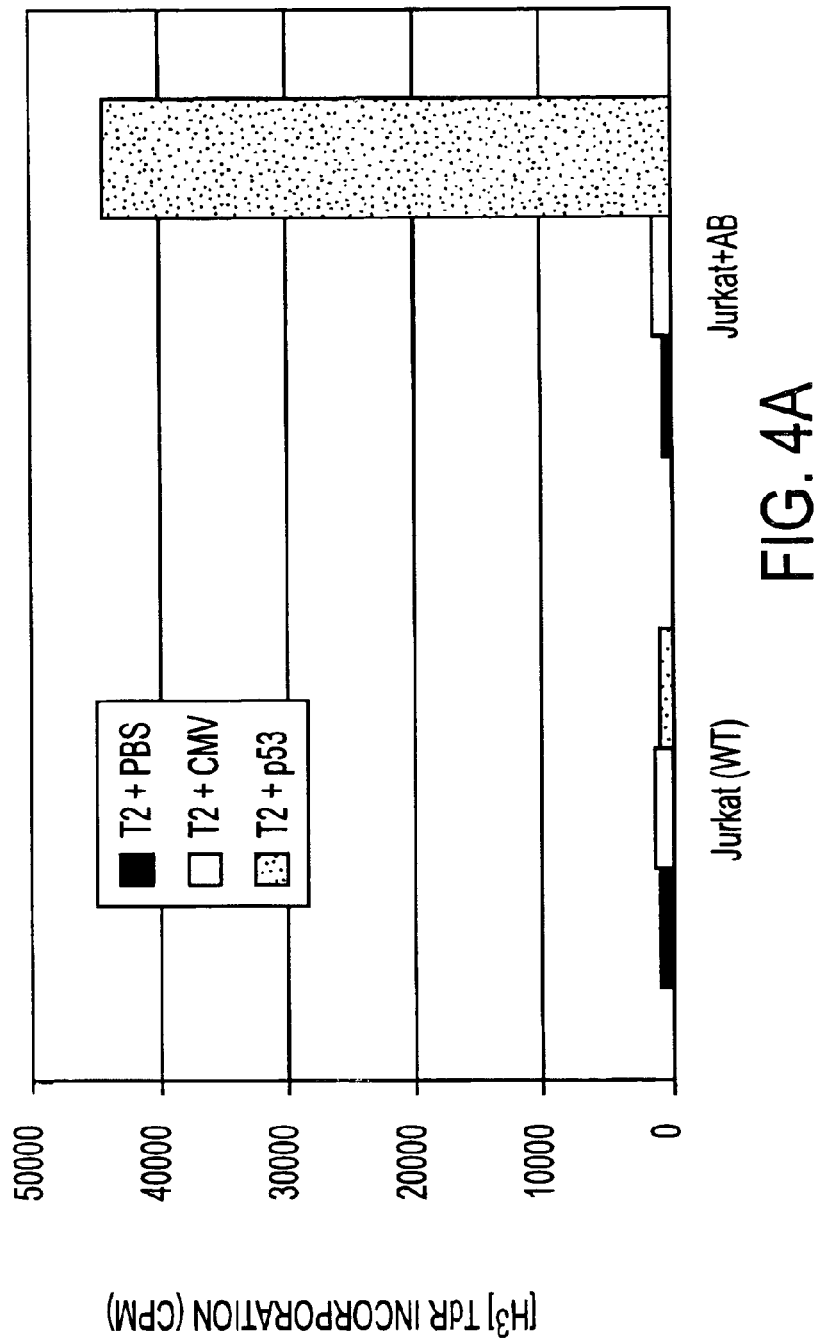
FIGS. 4A–4C show the function of the mu TCR A/B transfected Jurkat cells.
Figure 4B:
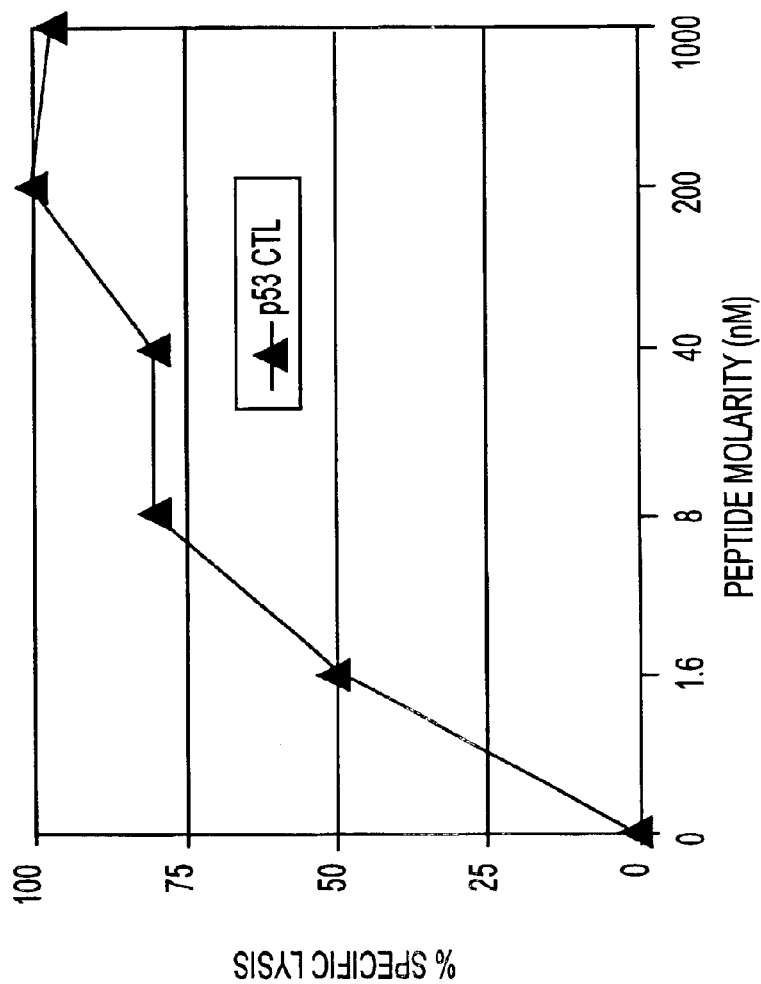
Figure 4C:
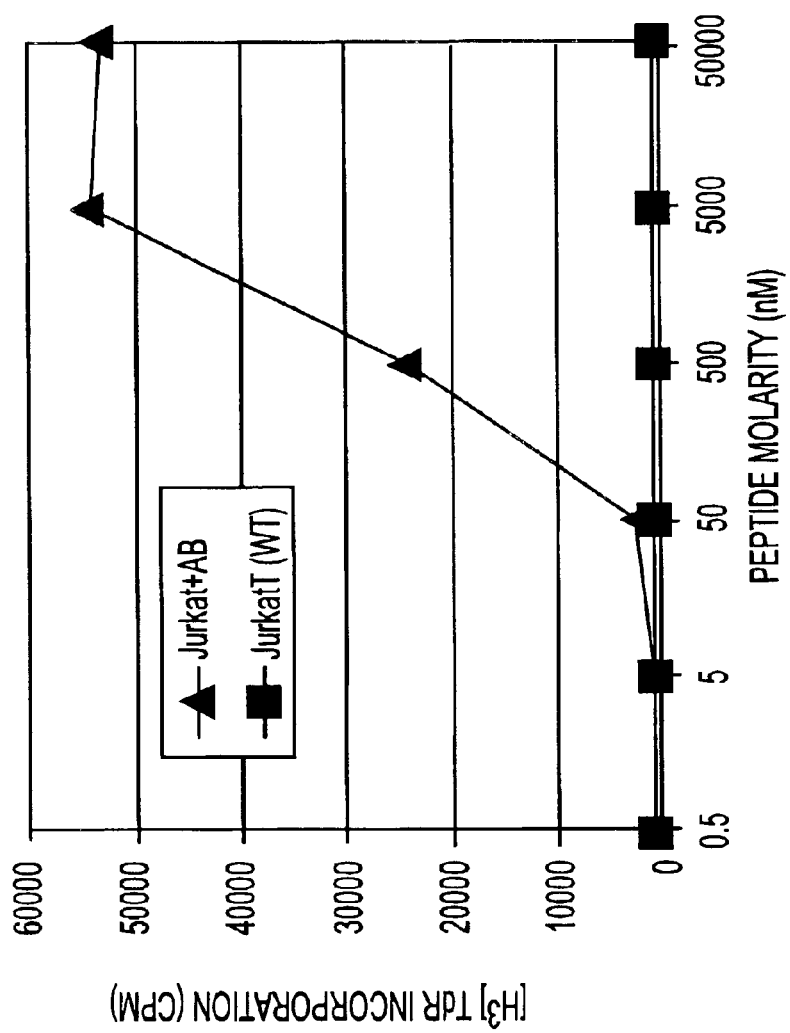

To determine whether doubly muTCR-transfected Jurkat T cells would still recognize the HLA A*0201 restricted T cell epitope from hu p53, the transfectants were incubated with T2 cells that were sensitized with a saturating concentration of hup53$_{149-157}$ peptide. In order to distinguish between specific and non-specific recognition, an HLA A*0201 epitope derived from CMV pp65 ((Diamond et al., *Blood*, 90:1751–1767, 1997), which is not recognized by the parental mu CTL 3A3/3C9, was also used to sensitize T2 cells (FIG. 4A). To quantitate the extent of activation caused by recognition of the peptide epitope, the release of IL-2 by the transfectants was utilized. The results show specific recognition by the Jurkat T cell transfectant of the hup53$_{149-157}$ CTL epitope bound to T2 cells with a vigorous response, as measured by $^3$H-Thymidine incorporation in CTLL-2 cells. Further demonstration of the specificity of the recognition, are the results of the parallel analysis of the untransfected parental T cell line incubated with T2 cells sensitized by the same peptides. No significant IL-2 production was measured, in contrast with the mu TCR transfectant. As T2 cells efficiently present exogenous peptide, the question arose whether the sensitivity of the transfectant to epitope concentration was similar to the parental 3A3/3C9 mu CD8$^+$ CTL clone (FIG. 4B). Therefore, a titration of the hu p53$_{149-157}$ T cell epitope was conducted using a T cell transfectant clone compared to parental Jurkat T cells. The half maximum concentration of activation of the clone is approximately 500 nM peptide (FIG. 4C). This concentration of peptide for half maximal stimulation is approximately 250-fold greater than what is needed to activate cytolysis by the parental mu CD$^{8+}$ CTL (FIG. 4B). The difference in level of peptide sensitivity is what might be expected of a transfectant line that contained multiple different TCR heterodimers as a result of independent association of all four expressed hu and mu TCR chains. It seems that the degree of activation is sufficient that the transfectant may still recognize lesser amounts of hu p53$_{149-157}$, as is found in cell lines which express a diverse repertoire of endogenous peptides, in contrast to T2 cells. However, it would require a direct test of recognition of the endogenously processed hu p53, to determine whether smaller amounts of epitope could be recognized by the transfectant and cause its activation and IL-2 production.

Example 7

Endogenous Processing of Hu p53 Causes the Activation of mu TCR Transfected Jurkat T Cells Earlier reports had shown that a transfected TCR, either mu or hu, would still be capable of recognition of endogenously processed epitope in a transfected APC (Dembic et al., *Nature* 320:232–238, 1986). In terms of hu tumor antigens, examples exist in which peptide epitope sensitized APC were recognized by a TCR transfectant (Cole, et al., *Cancer Res.*, 55:748–752, 1995). Nonetheless, there is only a single example of recognition of an endogenously processed hu tumor antigen utilizing either a hu transfected TCR, and none as of yet for mu transfected TCR (Clay et al., *J. Immunol.*, 163:507–513, 1999). The recognition of endogenously processed hu p53 molecule represents a testable model to determine whether the mu TCR specific for a wt epitope of hu p53 would recognize a hu tumor cell which over expressed p53. It has been previously shown that the osteosarcoma cell line SAOS transfected with a hu p53 vector expressing a mutant hu p53 molecule is well recognized by the muCTL clone 3A3/3C9 (McCarty et al., supra). The question whether the muTCR transfected Jurkat T cell would also recognize the SAOS/p53 and undergo activation and IL-2 production was posed. Therefore, experiments almost identical to the previous T2 epitope sensitization experiments were conducted, this time utilizing the endogenous processing of p53 as a means to generate sensitizing epitope.

From previous studies, it was known that the intensity of recognition of the endogenously processed hu p53 may be far less than that using the synthetic CTL epitope (Uematsu et al., supra; McCarty et al., *Ann. Surg. Oncol.*, supra). Nonetheless, the transfected Saos cell line served as a convenient starting point in our dissection of the level of recognition of the transfected Jurkat T cell. Our initial results with co-incubation of the Saos/p53 cell line and Jurkat AB TCR transfectant were negative, despite the addition of IFN-γ+TNF-α, which were used to activate MHC Class I on the APC. Our assumption was that since the Jurkat T cell is likely derived from a CD4$^+$ thymocyte, and does not co-express CD8, it might be defective in its adhesion properties, when engaging a Class I expressing APC. As a result, the degree of activation may be far less than would be expected if the cell were a CTL which expressed CD8 and could better bind to the APC (Garcia et al., *Nature*, 384:577–581, 1996).

In order to compensate for inherent difficulties in APC recognition by the AB TCR transfectants the mAb 9.3 as a means to activate CD28 was utilized, in the hope of enhancing the sensitivity of the T cell transfectant towards endogenously processed p53 (Nunes et al., *Int. Immunol.*, 5:311–315, 1993. This strategy worked well using the parental Saos cell line as compared to the Saos cell line transfected with mutant hu p53 (FIG. 5). Incubation of the Jurkat T cell transfectant with the Saos cell lines resulted in the differential recognition of only the cell lines that expressed hu p53 (FIG. 5). The data show that the presence of hu p53, presumably in processed form, resulted in the activation of the co-incubated transfectant to produce IL-2. As one objective is to evaluate whether this mu TCR will effectively recognize endogenously processed mutant p53 in tumor cells, a series of hu tumors expressing HLA A*0201 and mutant forms of hu p53, as well as their counterparts, which did not express one or both of these molecules (FIG. 5) were surveyed. A similar assay was performed, using as a readout, the production of IL-2 as determined by quantitation of [$^3$H] Thymidine incorporation by the CTLL-2 cell line. We used A series of hu tumors described in Table 2 were used, and the correlation of production of IL-2 versus the expression of HLA A*0201 and hu p53 was examined. Two cells lines which expressed mutant forms of hu p53 were able to activate the transfectants (PANC-1, MDA-MB-231). Whereas, cell lines that either were p53$^-$ (Saos) or did not express HLA A*0201 (ASPC-1 and SK-BR3) were not able to activate the Jurkat T cell transfectant to produce IL-2. These data unequivocally demonstrate that the Jurkat T cell transfectant has been endowed with the property of recognition of processed hu p53 in the context of the HLA A*0201 molecule.

The approach in the present invention takes advantage of recent progress in cellular immunology, and involves the transfection of hu T cells with a TCR from cloned TAA-specific CTL. Chimeric receptors, introduced into T cells, which utilize the CD3ξ chain cytoplasmic domain and external ligand-binding domain from the V(D)J region of the A/B TCR are able to directly activate the transfected cell without CD3 expression (Eshhar et al.,*Proc Natl Acad Sci USA*, 90:720–724, 1993). This can result in lymphokine production (Th2 cell) or lytic function (CTL) (Id.). As a preliminary step to the generation of a single chain TCR construct for immunogene therapy, it is necessary to demonstrate the function of the TCR of interest in a readily transfected hu T cell line. This same strategy was recently utilized by Cole et al, who transfected Jurkat cells with a cloned T-cell receptor from MART-1 specific hu CTL (Cole et al., *Cancer Res.*, 55:748–752, 1995). The resulting transfectants were able to recognize and secrete cytokine in response to challenge with the peptide transporter mutant cell, T2 pulsed with the appropriate peptide epitope. However, unlike our own data with the p53-specific TCR, when the MART-1-specific transfectants were challenged with bona-fide melanoma cells expressing the same antigen, they were unable to direct the T cells to secrete cytokine or lyse them. This unexpected result may occur because MART-1, like p53, is expressed during normal hu development, and normal tolerance mechanisms in the thymus may cause the elimination of T cells expressing TCRs which recognize the antigen with high affinity(negative selection). These tolerance mechanisms may be overcome through the xenogeneic transfer of antigen specific TCR from mu to hu T cells.

The above Examples show that p53 specific mu TCR will function in the hu CD4$^+$ T cell line, Jurkat. The transfer of functional mu TCR not only results in the rescue of hu CD3 expression in TCR mutant forms of Jurkat, but transfers antigen recognition from the mu TCR to the hu line. Peptide recognition and secretion of cytokine by the TCR modified Jurkat in response to peptide pulsed T2 cells was vigorous. Demonstrating that the TCR modified Jurkat recognized endogenously processed antigen on p53 overexpressing cells, was more difficult. The Jurkat line was used in these studies because it is one of the few stable hu T cell lines that can be readily transfected. However, it may not be the best model to study high density TCR expression because of the presence of an endogenous and functional TCR heterodimer, and the significantly lower expression of TCR chains as compared to normal T cells (Diamond et al., *J. Exp. Med.*, 174:229–241, 1991). These deficits were overcome by optimizing antigen presentation in the tumor cell targets through the preincubation of target cells with IFN-γ and TNF-α.

Recognition of tumor cells by the TCR modified Jurkat required interaction between the modified CD4$^+$ T helper line and processed p53 presented by MHC class I on the hu tumor cells. This occurred without the added stabilizing interaction of the MHC Class I heavy chain domain, α3 on the tumor cells, with the T cell co-receptor, CD8 (Norment et al., *Nature*, 336:79–81, 1988), which is absent in Jurkat. Generating A and B TCR Jurkat transfectants which also express CD8 would require a triple transfection which might be difficult due to the relative instability of the mu-A/B TCR Jurkat line. To overcome the inherent inadequacies of Jurkat cells as functional effectors following mu-A/B TCR transfer, additional costimulation was provided by preincubating the TCR modified Jurkat cells with a monoclonal antibody recognizing CD28 (mAb9.3) (Pierres et al., *Eur. J. Immunol.*, 18:685–690, 1988). This particular monoclonal antibody was chosen because of its known agonist activity on CD28$^+$ Jurkat T cells. In the well controlled experiments described here, the CD28 stimulated Jurkat secrete IL-2 only in response to appropriate HLA A*0201$^+$, p53 over-expressing APCs (FIG. 5).

The strategy of ex-vivo expansion and adoptive immunotherapy using antigen specific CTLs has been under investigation for several years with mixed results. Initial attempts at adoptive CTL transfer were hindered by technical difficulty in generating large numbers of CTLs with defined specificity. These difficulties have been largely overcome. The efficacy of adoptive T cell therapy has been successfully demonstrated recently in clinical trials utilizing the adoptive transfer of large numbers of EBV (Rooney et al. *Blood*, 92:1549–1555, 1998) or CMV (Walter et al., *N. Eng. J. Med.*, 333:1038–1044, 1995) specific CTL. Translation of these promising results to the adoptive immunotherapy of malignancy will be difficult because, unlike viral antigens, most tumor associated antigens are expressed on normal cells and are subject to tolerance. Our demonstration that high affinity tumor p53 specificity can be transferred from mu to hu T cells should encourage efforts to apply xenogeneic TCR transfer for the immunotherapy of poorly immunogenic tumors.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. An isolated nucleic acid which encodes a human p53 specific HLA restricted murine T-cell receptor (TCR), wherein said nucleic acid comprises
   (a) a polynucleotide encoding the A chain of a hu p53-specific, HLA restricted mu T cell receptor (TCR), said A chain having the amino acid sequence set forth in SEQ ID NO:19; and
   (b) a polynucleotide encoding the B chain of a hu p53-specific, HLA restricted mu TCR, said B chain having the amino acid sequence set forth in SEQ ID NO:21.

2. An isolated nucleic acid selected from the group consisting of:
   (a) a polynucleotide encoding the A chain of a hu p53-specific, HLA restricted mu T cell receptor (TCR), said A chain having the amino acid sequence set forth in SEQ ID NO:19; and
   (b) a polynucleotide encoding the B chain of a hu p53-specific, HLA restricted mu TCR, said B chain having the amino acid sequence set forth in SEQ ID NO:21.

3. The nucleic acid of claim 1, wherein the polynucleotides are operably linked to a transcription control element.

4. A vector which comprises the nucleic acid of claim 1.

5. The vector of claim 4, wherein said vector is an expression vector.

6. A vector which comprises the nucleic acid of claim 3.

7. An isolated hu CD8$^+$ cytotoxic T lymphocyte which is transfected with one or more nucleic acids which express a hu p53-specific, HLA restricted mu TCR, wherein said nucleic acids comprise
   (a) a polynucleotide encoding the A chain of a hu p53-specific, HLA restricted mu T cell receptor (TCR), said A chain having the amino acid sequence set forth in SEQ ID NO:19; and
   (b) a polynucleotide encoding the B chain of a hu p53-specific, HLA restricted mu TCR, said B chain having the amino acid sequence set forth in SEQ ID NO:21.

8. An adoptive immunotherapy method of treating an individual who has a tumor that is HLA A*0201 and over-expresses p53 which comprises administering to the individual an effective amount of CD8$^{30}$ cytotoxic T lymphocytes of claim 7, wherein the T-lymphocytes are autologous T lymphocytes and wherein cells of said tumor are lysed.

* * * * *

SEQUENCE LISTING

<160> NUMBER OF SEQ ID NOS: 21

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
catagctttc atgtccagca cag                                          23

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
ctcctgctac tgtgtgtatt gagc                                         24

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
gtgctgtcct gagaccgagg atc                                          23

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
tctctaccag atgctgattc taagcct                                      27

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
tggtcgactc aactggacca cag                                          23

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
gacctccttg ccattcac                                                18

<210> SEQ ID NO 7
<211> LENGTH: 18
<212> TYPE: DNA

```
<213> ORGANISM: Artificial Sequence
<220> FEATURE:
<223> OTHER INFORMATION: Primer

<400> SEQUENCE: 7
accatcctca tgagatcc                                                       18

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
gaccttgggt ggagtcacat ttctcagatc                                          30

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
actctagatg ggctccagac tc                                                  22

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
cagtcgacat aaaagtttgt ctcagg                                              26

<210> SEQ ID NO 11
<211> LENGTH: 7
<212> TYPE: PRT
<213> ORGANISM: Mus musculus

<400> SEQUENCE: 11

Val Tyr Phe Cys Ala Met Arg
1               5

<210> SEQ ID NO 12
<211> LENGTH: 19
<212> TYPE: PRT
<213> ORGANISM: Mus musculus

<400> SEQUENCE: 12

Asp Thr Asn Ala Tyr Lys Val Ile Phe Gly Lys Gly Thr His Leu His
1               5                   10                  15

Val Leu Pro

<210> SEQ ID NO 13
<211> LENGTH: 7
<212> TYPE: PRT
<213> ORGANISM: Mus musculus

<400> SEQUENCE: 13

Asn Ile Gln Asn Pro Glu Pro
1               5
```

<210> SEQ ID NO 14
<211> LENGTH: 8
<212> TYPE: PRT
<213> ORGANISM: Mus musculus

<400> SEQUENCE: 14

Ala Val Tyr Phe Cys Ala Ser Ser
1               5

<210> SEQ ID NO 15
<211> LENGTH: 3
<212> TYPE: PRT
<213> ORGANISM: Mus musculus

<400> SEQUENCE: 15

Pro Ser Ser
1

<210> SEQ ID NO 16
<211> LENGTH: 14
<212> TYPE: PRT
<213> ORGANISM: Mus musculus

<400> SEQUENCE: 16

Tyr Glu Gln Tyr Phe Gly Pro Gly Ile Arg Leu Thr Val Leu
1               5                   10

<210> SEQ ID NO 17
<211> LENGTH: 9
<212> TYPE: PRT
<213> ORGANISM: Mus musculus

<400> SEQUENCE: 17

Glu Asp Leu Arg Asn Val Thr Pro Pro
1               5

<210> SEQ ID NO 18
<211> LENGTH: 844
<212> TYPE: DNA
<213> ORGANISM: Mus musculus
<220> FEATURE:
<221> NAME/KEY: CDS
<222> LOCATION: (11)..(826)

<400> SEQUENCE: 18

```
tctctagacc atg ctg att cta agc ctg ttg gga gca gcc ttt ggc tcc         49
           Met Leu Ile Leu Ser Leu Leu Gly Ala Ala Phe Gly Ser
               1               5                   10 att tgt ttt gca gca acc agc atg gcc cag aag gta aca cag act cag        97
Ile Cys Phe Ala Ala Thr Ser Met Ala Gln Lys Val Thr Gln Thr Gln
    15                  20                  25 act tca att tct gtg gtg gag aag aca acg gtg aca atg gac tgt gtg       145
Thr Ser Ile Ser Val Val Glu Lys Thr Thr Val Thr Met Asp Cys Val
30                  35                  40                  45 tat gaa acc cgg gac agt tct tac ttc tta ttc tgg tac aag caa aca       193
Tyr Glu Thr Arg Asp Ser Ser Tyr Phe Leu Phe Trp Tyr Lys Gln Thr
                50                  55                  60 gca agt ggg gaa ata gtt ttc ctt att cgt cag gac tct tac aaa aag       241
Ala Ser Gly Glu Ile Val Phe Leu Ile Arg Gln Asp Ser Tyr Lys Lys
            65                  70                  75 gaa aat gca aca gtg ggt cat tat tct ctg aac ttt cag aag cca aaa       289
Glu Asn Ala Thr Val Gly His Tyr Ser Leu Asn Phe Gln Lys Pro Lys
        80                  85                  90
```

-continued

```
agt tcc atc gga ctc atc atc acc gcc aca cag att gag gac tca gca      337
Ser Ser Ile Gly Leu Ile Ile Thr Ala Thr Gln Ile Glu Asp Ser Ala
     95                 100                 105 gta tat ttc tgt gct atg agg gac aca aat gct tac aaa gtc atc ttt      385
Val Tyr Phe Cys Ala Met Arg Asp Thr Asn Ala Tyr Lys Val Ile Phe
110                 115                 120                 125 gga aaa ggg aca cat ctt cat gtt ctc cct aac atc cag aac cca gaa      433
Gly Lys Gly Thr His Leu His Val Leu Pro Asn Ile Gln Asn Pro Glu
                130                 135                 140 cct gct gtg tac cag tta aaa gat cct cgg tct cag gac agc acc ctc      481
Pro Ala Val Tyr Gln Leu Lys Asp Pro Arg Ser Gln Asp Ser Thr Leu
            145                 150                 155 tgc ctg ttc acc gac ttt gac tcc caa atc aat gtg ccg aaa acc atg      529
Cys Leu Phe Thr Asp Phe Asp Ser Gln Ile Asn Val Pro Lys Thr Met
        160                 165                 170 gaa tct gga acg ttc atc act gac aaa act gtg ctg gac atg aaa gct      577
Glu Ser Gly Thr Phe Ile Thr Asp Lys Thr Val Leu Asp Met Lys Ala
    175                 180                 185 atg gat tcc aag agc aat ggg gcc att gcc tgg agc aac cag aca agc      625
Met Asp Ser Lys Ser Asn Gly Ala Ile Ala Trp Ser Asn Gln Thr Ser
190                 195                 200                 205 ttc acc tgc caa gat atc ttc aaa gag acc aac gcc acc tac ccc agt      673
Phe Thr Cys Gln Asp Ile Phe Lys Glu Thr Asn Ala Thr Tyr Pro Ser
                210                 215                 220 tca gac gtt ccc tgt gat gcc acg ttg acc gag aaa agc ttt gaa aca      721
Ser Asp Val Pro Cys Asp Ala Thr Leu Thr Glu Lys Ser Phe Glu Thr
            225                 230                 235 gat atg aac cta aac ttt caa aac ctg tca gtt atg gga ctc cga atc      769
Asp Met Asn Leu Asn Phe Gln Asn Leu Ser Val Met Gly Leu Arg Ile
        240                 245                 250 ctc ctg ctg aaa gta gcg gga ttt aac ctc ctc atg acg ctg agg ctg      817
Leu Leu Leu Lys Val Ala Gly Phe Asn Leu Leu Met Thr Leu Arg Leu
    255                 260                 265 tgg tcc agt tgaggtctgc aagactga                                      844
Trp Ser Ser
270
```

<210> SEQ ID NO 19
<211> LENGTH: 272
<212> TYPE: PRT
<213> ORGANISM: Mus musculus

<400> SEQUENCE: 19

```
Met Leu Ile Leu Ser Leu Leu Gly Ala Ala Phe Gly Ser Ile Cys Phe
1               5                   10                  15

Ala Ala Thr Ser Met Ala Gln Lys Val Thr Gln Thr Gln Thr Ser Ile
            20                  25                  30

Ser Val Val Glu Lys Thr Thr Val Thr Met Asp Cys Val Tyr Glu Thr
        35                  40                  45

Arg Asp Ser Ser Tyr Phe Leu Phe Trp Tyr Lys Gln Thr Ala Ser Gly
    50                  55                  60

Glu Ile Val Phe Leu Ile Arg Gln Asp Ser Tyr Lys Lys Glu Asn Ala
65                  70                  75                  80

Thr Val Gly His Tyr Ser Leu Asn Phe Gln Lys Pro Lys Ser Ser Ile
                85                  90                  95

Gly Leu Ile Ile Thr Ala Thr Gln Ile Glu Asp Ser Ala Val Tyr Phe
            100                 105                 110

Cys Ala Met Arg Asp Thr Asn Ala Tyr Lys Val Ile Phe Gly Lys Gly
        115                 120                 125
```

```
Thr His Leu His Val Leu Pro Asn Ile Gln Asn Pro Glu Pro Ala Val
    130                 135                 140

Tyr Gln Leu Lys Asp Pro Arg Ser Gln Asp Ser Thr Leu Cys Leu Phe
145                 150                 155                 160

Thr Asp Phe Asp Ser Gln Ile Asn Val Pro Lys Thr Met Glu Ser Gly
                165                 170                 175

Thr Phe Ile Thr Asp Lys Thr Val Leu Asp Met Lys Ala Met Asp Ser
            180                 185                 190

Lys Ser Asn Gly Ala Ile Ala Trp Ser Asn Gln Thr Ser Phe Thr Cys
        195                 200                 205

Gln Asp Ile Phe Lys Glu Thr Asn Ala Thr Tyr Pro Ser Ser Asp Val
    210                 215                 220

Pro Cys Asp Ala Thr Leu Thr Glu Lys Ser Phe Glu Thr Asp Met Asn
225                 230                 235                 240

Leu Asn Phe Gln Asn Leu Ser Val Met Gly Leu Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 20
<211> LENGTH: 916
<212> TYPE: DNA
<213> ORGANISM: Mus musculus
<220> FEATURE:
<221> NAME/KEY: CDS
<222> LOCATION: (8)..(913)

<400> SEQUENCE: 20 actctag atg ggc tcc aga ctc ttc ttt gtg gtt ttg att ctc ctg tgt       49
        Met Gly Ser Arg Leu Phe Phe Val Val Leu Ile Leu Leu Cys
        1               5                   10 gca aaa cac atg gag gct gca gtc acc caa agt cca aga agc aag gtg       97
Ala Lys His Met Glu Ala Ala Val Thr Gln Ser Pro Arg Ser Lys Val
15                  20                  25                  30 gca gta aca gga gga aag gtg aca ttg agc tgt cac cag act aat aac      145
Ala Val Thr Gly Gly Lys Val Thr Leu Ser Cys His Gln Thr Asn Asn
                35                  40                  45 cat gac tat atg tac tgg tat cgg cag gac acg ggg cat ggg ctg agg      193
His Asp Tyr Met Tyr Trp Tyr Arg Gln Asp Thr Gly His Gly Leu Arg
            50                  55                  60 ctg atc cat tac tca tat gtc gct gac agc acg gag aaa gga gat atc      241
Leu Ile His Tyr Ser Tyr Val Ala Asp Ser Thr Glu Lys Gly Asp Ile
        65                  70                  75 cct gat ggg tac aag gcc tcc aga cca agc caa gag aat ttc tct ctc      289
Pro Asp Gly Tyr Lys Ala Ser Arg Pro Ser Gln Glu Asn Phe Ser Leu
    80                  85                  90 att ctg gag ttg gct tcc ctt tct cag aca gct gta tat ttc tgt gcc      337
Ile Leu Glu Leu Ala Ser Leu Ser Gln Thr Ala Val Tyr Phe Cys Ala
95                  100                 105                 110 agc agt cct tcc tcc tat gaa cag tac ttc ggt ccc ggc acc agg ctc      385
Ser Ser Pro Ser Ser Tyr Glu Gln Tyr Phe Gly Pro Gly Thr Arg Leu
                115                 120                 125 acg gtt tta gag gat ctg aga aat gtg act cca ccc aag gtc tcc ttg      433
Thr Val Leu Glu Asp Leu Arg Asn Val Thr Pro Pro Lys Val Ser Leu
            130                 135                 140 ttt gag cca tca aaa gca gag att gca aac aaa caa aag gct acc ctc      481
Phe Glu Pro Ser Lys Ala Glu Ile Ala Asn Lys Gln Lys Ala Thr Leu
        145                 150                 155
```

```
                                                                -continued gtg tgc ttg gcc agg ggc ttc ttc cct gac cac gtg gag ctg agc tgg     529
Val Cys Leu Ala Arg Gly Phe Phe Pro Asp His Val Glu Leu Ser Trp
    160             165                 170 tgg gtg aat ggc aag gag gtc cac agt ggg gtc agc acg gac cct cag     577
Trp Val Asn Gly Lys Glu Val His Ser Gly Val Ser Thr Asp Pro Gln
175             180                 185                 190 gcc tac aag gag agc aat tat agc tac tgc ctg agc agc cgc ctg agg     625
Ala Tyr Lys Glu Ser Asn Tyr Ser Tyr Cys Leu Ser Ser Arg Leu Arg
                195                 200                 205 gtc tct gct acc ttc tgg cac aat cct cga aac cac ttc cgc tgc caa     673
Val Ser Ala Thr Phe Trp His Asn Pro Arg Asn His Phe Arg Cys Gln
            210                 215                 220 gtg cag ttc cat ggg ctt tca gag gag gac aag tgg cca gag ggc tca     721
Val Gln Phe His Gly Leu Ser Glu Glu Asp Lys Trp Pro Glu Gly Ser
        225                 230                 235 ccc aaa cct gtc aca cag aac atc agt gca gag gcc tgg ggc cga gca     769
Pro Lys Pro Val Thr Gln Asn Ile Ser Ala Glu Ala Trp Gly Arg Ala
    240                 245                 250 gac tgt gga atc act tca gca tcc tat cat cag ggg gtt ctg tct gca     817
Asp Cys Gly Ile Thr Ser Ala Ser Tyr His Gln Gly Val Leu Ser Ala
255                 260                 265                 270 acc atc ctc tat gag atc cta ctg ggg aag gcc acc cta tat gct gtg     865
Thr Ile Leu Tyr Glu Ile Leu Leu Gly Lys Ala Thr Leu Tyr Ala Val
                275                 280                 285 ctg gtc agt ggc ctg gtg ctg atg gcc atg gtc aag aaa aaa aat tcc     913
Leu Val Ser Gly Leu Val Leu Met Ala Met Val Lys Lys Lys Asn Ser
            290                 295                 300 tga                                                                 916

<210> SEQ ID NO 21
<211> LENGTH: 302
<212> TYPE: PRT
<213> ORGANISM: Mus musculus

<400> SEQUENCE: 21

Met Gly Ser Arg Leu Phe Phe Val Val Leu Ile Leu Cys Ala Lys
1               5                   10                  15

His Met Glu Ala Ala Val Thr Gln Ser Pro Arg Ser Lys Val Ala Val
                20                  25                  30

Thr Gly Gly Lys Val Thr Leu Ser Cys His Gln Thr Asn Asn His Asp
            35                  40                  45

Tyr Met Tyr Trp Tyr Arg Gln Asp Thr Gly His Gly Leu Arg Leu Ile
        50                  55                  60

His Tyr Ser Tyr Val Ala Asp Ser Thr Glu Lys Gly Asp Ile Pro Asp
65                  70                  75                  80

Gly Tyr Lys Ala Ser Arg Pro Ser Gln Glu Asn Phe Ser Leu Ile Leu
                85                  90                  95

Glu Leu Ala Ser Leu Ser Gln Thr Ala Val Tyr Phe Cys Ala Ser Ser
                100                 105                 110

Pro Ser Ser Tyr Glu Gln Tyr Phe Gly Pro Gly Thr Arg Leu Thr Val
            115                 120                 125

Leu Glu Asp Leu Arg Asn Val Thr Pro Pro Lys Val Ser Leu Phe Glu
        130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175
```

```
                              -continued

Asn Gly Lys Glu Val His Ser Gly Val Ser Thr Asp Pro Gln Ala Tyr
            180             185              190

Lys Glu Ser Asn Tyr Ser Tyr Cys Leu Ser Ser Arg Leu Arg Val Ser
        195             200             205

Ala Thr Phe Trp His Asn Pro Arg Asn His Phe Arg Cys Gln Val Gln
    210             215             220

Phe His Gly Leu Ser Glu Glu Asp Lys Trp Pro Glu Gly Ser Pro Lys
225             230             235             240

Pro Val Thr Gln Asn Ile Ser Ala Glu Ala Trp Gly Arg Ala Asp Cys
            245             250             255

Gly Ile Thr Ser Ala Ser Tyr His Gln Gly Val Leu Ser Ala Thr Ile
            260             265             270

Leu Tyr Glu Ile Leu Leu Gly Lys Ala Thr Leu Tyr Ala Val Leu Val
        275             280             285

Ser Gly Leu Val Leu Met Ala Met Val Lys Lys Lys Asn Ser
    290             295             300
```